US007696370B2

(12) United States Patent
Suppes et al.

(10) Patent No.: US 7,696,370 B2
(45) Date of Patent: Apr. 13, 2010

(54) SOY BASED POLYOLS

(75) Inventors: Galen Suppes, Columbia, MO (US); Fu-hung Hsieh, Columbia, MO (US); Yuan-Chan Tu, Columbia, MO (US); Pimphan Kiatsimkul, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 11/746,445

(22) Filed: May 9, 2007

(65) Prior Publication Data

US 2007/0265459 A1 Nov. 15, 2007

Related U.S. Application Data

(60) Provisional application No. 60/799,061, filed on May 9, 2006, provisional application No. 60/857,438, filed on Nov. 7, 2006.

(51) Int. Cl.
*C09F 7/00* (2006.01)
*C07C 2/02* (2006.01)
*C08G 63/91* (2006.01)

(52) U.S. Cl. .......................... 554/24; 585/507; 585/361

(58) Field of Classification Search ................... 525/10; 554/9, 161, 172, 24; 585/361, 350, 507
See application file for complete search history.

(56) References Cited

U.S. PATENT DOCUMENTS

| | | | | |
|---|---|---|---|---|
| 2,611,788 | A * | 9/1952 | Bloch Herman S | 585/361 |
| 3,827,993 | A | 8/1974 | Cunningham et al. | |
| 4,530,938 | A | 7/1985 | White | |
| 4,717,738 | A | 1/1988 | Fukuda et al. | |
| 4,831,076 | A | 5/1989 | Lidy et al. | |
| 5,374,446 | A | 12/1994 | Ferenz et al. | |
| 5,482,980 | A | 1/1996 | Pcolinsky | |
| 6,258,869 | B1 | 7/2001 | Shah et al. | |
| 6,399,698 | B1 | 6/2002 | Petrovic et al. | |
| 6,476,244 | B2 | 11/2002 | Mahlum | |
| 6,686,435 | B1 * | 2/2004 | Petrovic et al. | 528/44 |
| 6,759,542 | B2 | 7/2004 | Mahlum | |
| 2002/0095007 | A1 | 7/2002 | Larock et al. | |
| 2006/0041157 | A1 | 2/2006 | Petrovic et al. | |
| 2006/0178456 | A1 | 8/2006 | Seats et al. | |
| 2008/0281071 | A1 | 11/2008 | Ionescu et al. | |

FOREIGN PATENT DOCUMENTS

WO 2007127379 A1 11/2007

OTHER PUBLICATIONS

Powers, P.O., Heat Bodying of Drying Oils, 1950, The Journal of the American Oil Chemists' Society, vol. 27, No. 11, pp. 468-472.*

Yerrakondreddygari, K., Polyols Made form Vegetable Oil and their Application, Graduate Thesis, Dec. 2005, University of Missouri-Columbia, pp. 1-110.*

(Continued)

*Primary Examiner*—Rosalynd Keys
*Assistant Examiner*—Yate' K Cutliff

(57) ABSTRACT

The invention provides processes for converting a vegetable oil to a polymer. In particular, the processing steps comprise bodying, epoxidation, hydrolysis, and oligomerization. These processes provide new processing paths for the formation of polyols for use in rigid foam and other applications.

13 Claims, 7 Drawing Sheets

OTHER PUBLICATIONS

Figure 1:
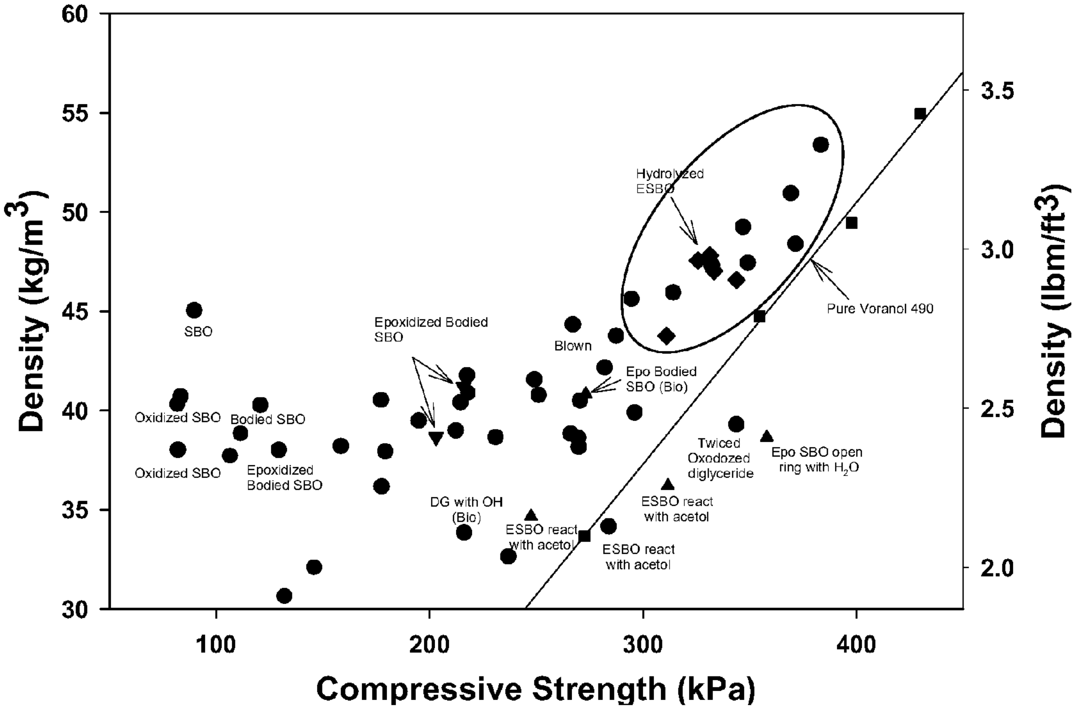

Radlove, S.B., et al., Comarative Evaluatio of Polymers of Heated-Bodied conjugated and Non-Conjugated Linseed and Soybean Oils.*

Dasari et al., "Low-pressure hydrogenolysis of glycerol to propylene glycol", Applied Catalysis A:General, 2005, pp. 225-231, vol. 281, Nos. 1-2.

Yerrakondreddygari; "Polyols made from Vegtable Oil and Their Applications", a thesis presented to the faculty of the Graduate School at University of Missouri—Colombia, 2005, Available to public Mar. 22, 2007.

International Search Report for PCT/US07/83694, dated Mar. 27, 2008; 3 pages.

* cited by examiner

SOY BASED POLYOLS

RELATED APPLICATIONS

This application claims benefit of priority to U.S. provisional application Ser. No. 60/799,061 filed May 9, 2006 and U.S. provisional application Ser. No. 60/857,438 filed Nov. 7, 2006, all of which are incorporated by reference herein.

FIELD OF INVENTION

This invention relates generally to processes for converting vegetable oil to polymers. More specifically, this invention relates to the conversion of soybean oil to polyols and the use of these polyols in polyurethanes.

BACKGROUND

Soy-based polyols are of interest because they are produced from renewable and domestic feed stocks rather than non-renewable petroleum-based feed stocks. Another advantage of soy-based polyols is the low cost of the feed stocks.

A variety of processes have been employed to produce polyols. Blown vegetable oils are an example of a soy-based polyol. U.S. Pat. Nos. 6,476,244 and 6,759,542 describe methods of synthesizing blown vegetable oils, which include use of air blown through the vegetable oils at elevated temperatures to promote partial oxidation. U.S. Pat. No. 6,686,435 describes a method of making natural oil-based polyols consisting of reacting the epoxy moiety of an epoxidized natural oil with an alcohol moiety of an alcohol in the presence of 10% to 30% water. U.S. Pat. No. 6,258,869 is on a process for production of polyols by reacting an agricultural feed stock with a multi-functional alcohol in the presence of a tin catalyst. U.S. Pat. No. 5,482,980 describe a method of preparing a flexible foam by using an epoxidized soybean oil at 7 to 25 parts by weight per hundred parts polyol.

A need, therefore, exists in the art for a process to convert vegetable oils to polyols of higher molecular weight than described in the prior art.

SUMMARY OF THE INVENTION

The presently disclosed process advances the art and overcomes problems on converting vegetable oils into polymers. The process produces polyols with unique and improved properties.

One aspect of the invention provides a process for converting an unsaturated molecule containing at least six carbon atoms to a polyfunctional oxygenate prepolymer. The process comprises bodying the unsaturated molecule at a temperature between 40° to 350° C. for less than 48 hours in an environment where diatomic oxygen is substantially absent to form an oligomer. The oligomer has a viscosity at least 20% greater than the viscosity of the unsaturated molecule. The process further comprises reacting the oligomer with an oxygen-containing molecule to form the polyfunctional oxygenate prepolymer.

Another aspect of the invention provides a process for converting an unsaturated molecule containing at least six carbon atoms to an oxygen-containing product. The process comprises bodying the unsaturated molecule to form a bodied product. The bodying occurring at a temperature between 150° to 350° C. for less than 48 hours in an environment where diatomic oxygen is substantially absent. The viscosity of the bodied product is at least 20% greater than the viscosity of the unsaturated molecule. The process further comprises partially oxidizing at least one carbon-carbon π-bond in the bodied product in a manner that attaches an oxygen-containing moiety to form the oxygen-containing product.

A further aspect of the invention encompasses a process for converting an unsaturated molecule containing at least six carbon atoms to an alcohol. The process comprises reacting at least one carbon-carbon π-bond of the unsaturated molecule with at least one monomer containing an oxygen-containing moiety at a temperature between 150° to 350° C. for less than 48 hours to form the alcohol.

Another aspect of the invention provides a B-side of a urethane formulation. The B-side comprising a molecular structure containing at least 30 carbon atoms, at least one alcohol moiety, and at least one epoxy moiety, wherein the molar ratio of epoxy to alcohol moieties in the B-side is between 1:3 and 1:0.5.

A still further aspect of the invention encompasses a process for synthesizing a polyol. The process comprising reacting a carboxylic acid having a carbon number at least 12 with an epoxy of a glyceride to form alcohol and ester moieties at the carbons of the epoxy moiety and a hydrocarbon chain containing at least 12 carbons.

Other aspects and features of the invention are described in more detail herein.

BRIEF DESCRIPTIONS OF DRAWINGS

FIG. 1 presents a comparison of the performance of several soy-based formulations with a commercially available petroleum-based polyol, Voranol 490 (line). The formulations used 50% Voranol 490 and 50% soy-based derivative in the B-side.

Figure 2:
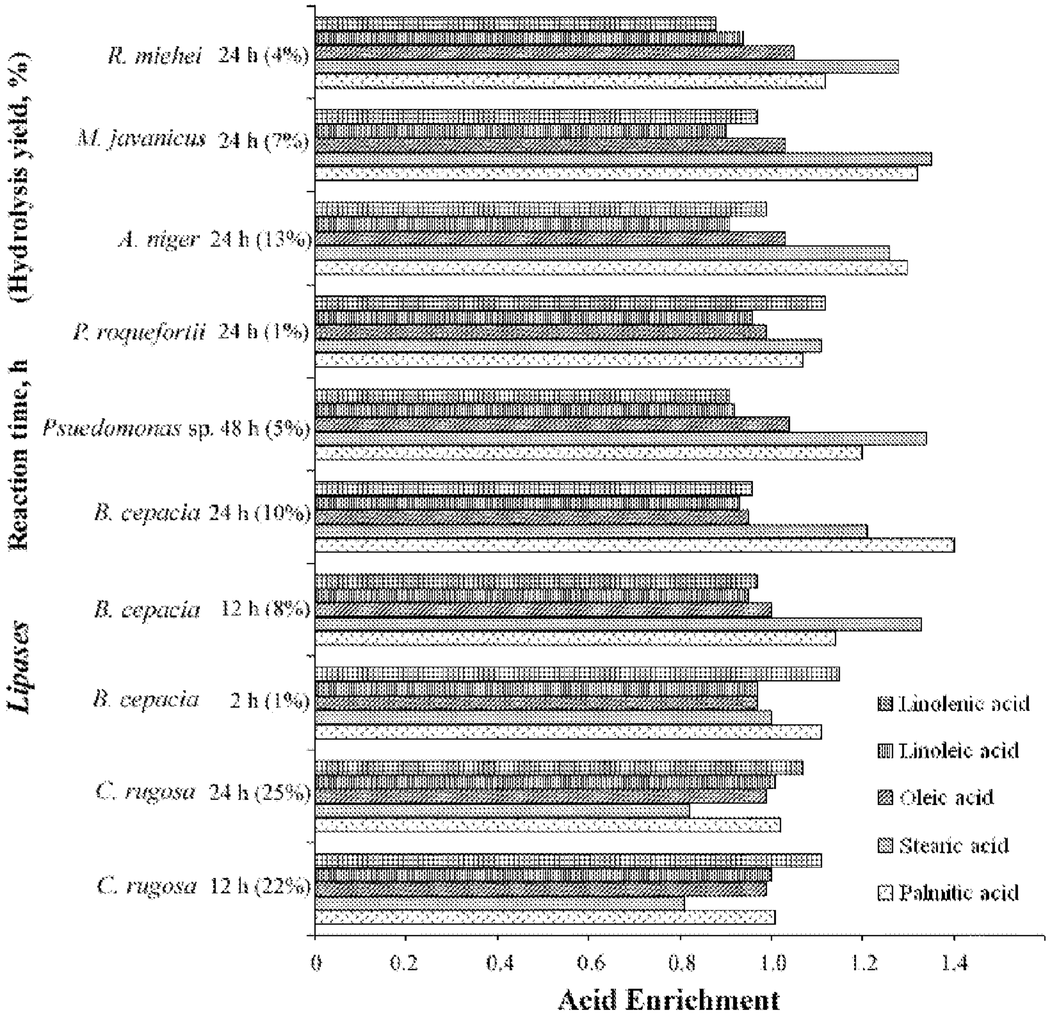

FIG. 2 presents the acid enrichment numbers of fatty acid products after enzymatic hydrolysis of soybean oil.

Figure 3:
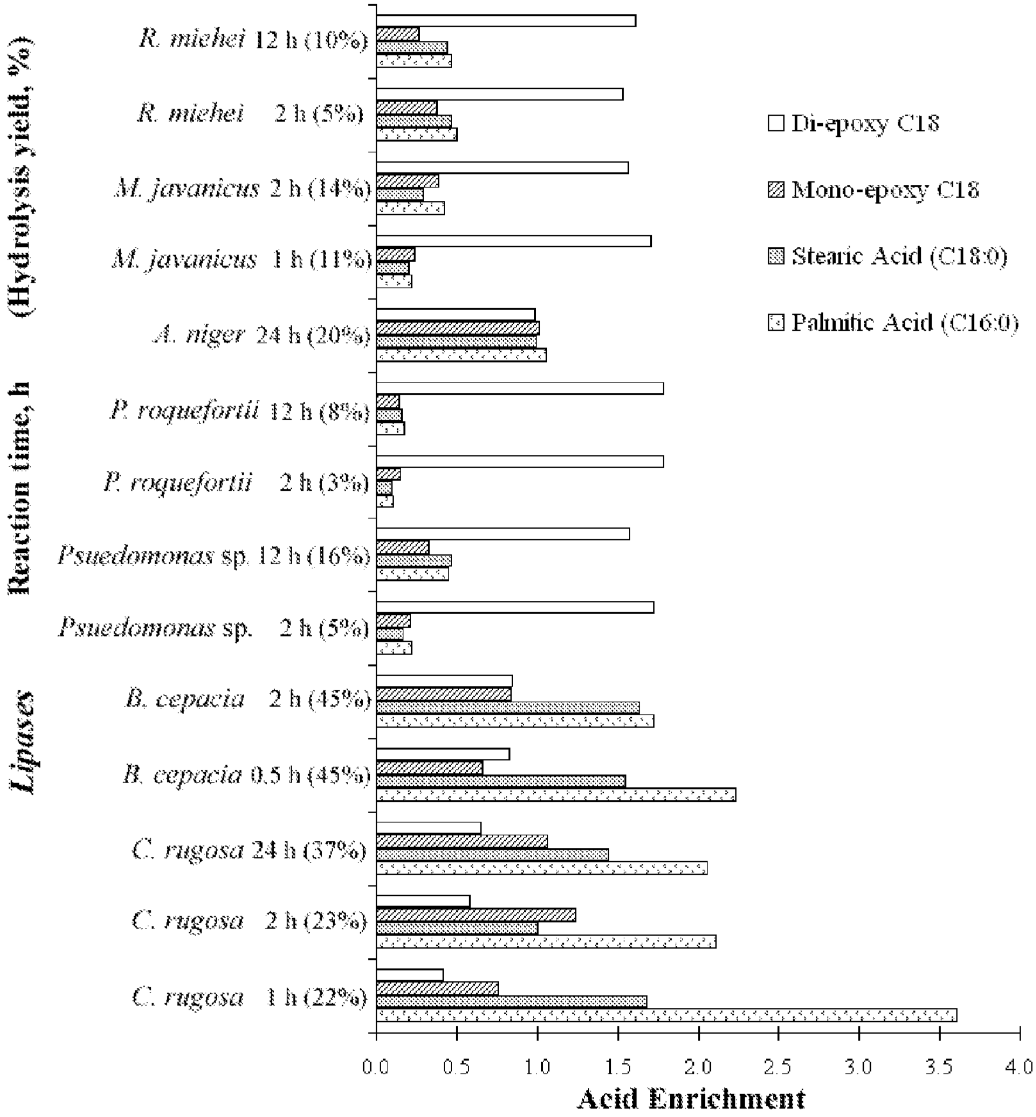

FIG. 3 presents the acid enrichment numbers of fatty acid products after enzymatic hydrolysis of epoxy soybean oil.

Figure 4:
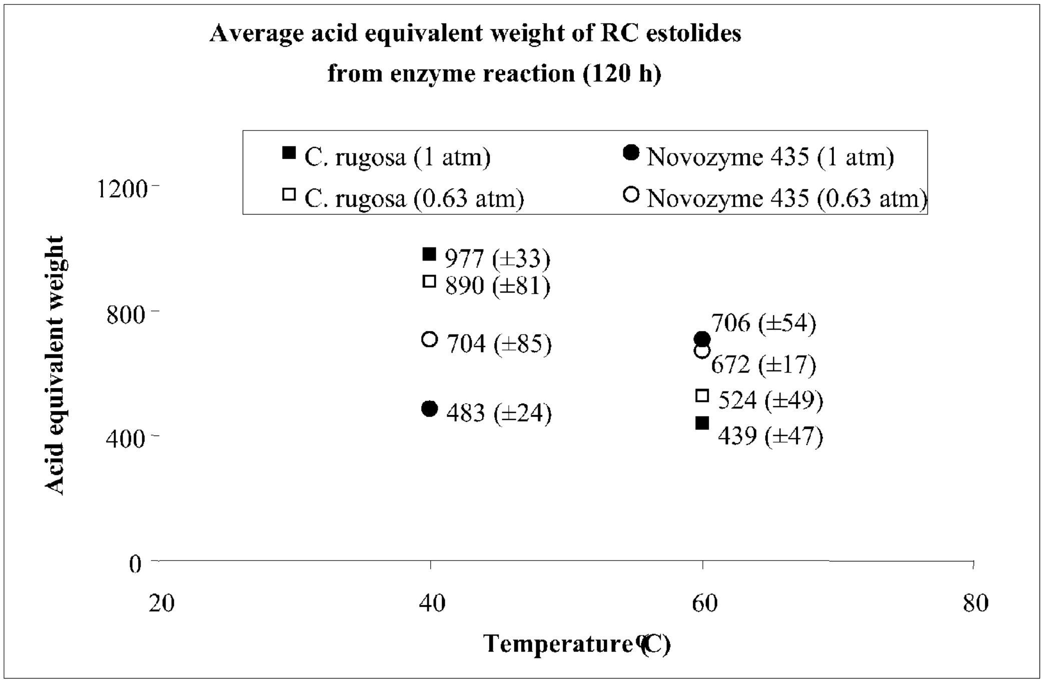

FIG. 4 presents the average acid equivalent weights of ricinoleic acid estolides after enzyme esterification (120 h).

Figure 5:
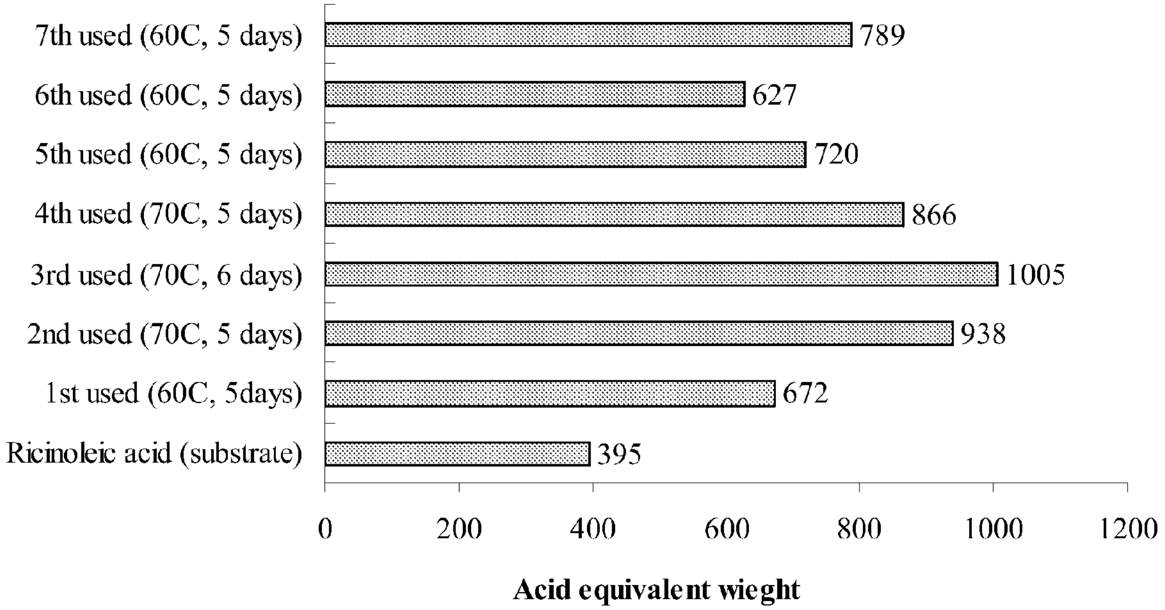

FIG. 5 illustrates the acid equivalent weights of ricinoleic acid estolides produced with recycled NOVOZYME 435®.

Figure 6:
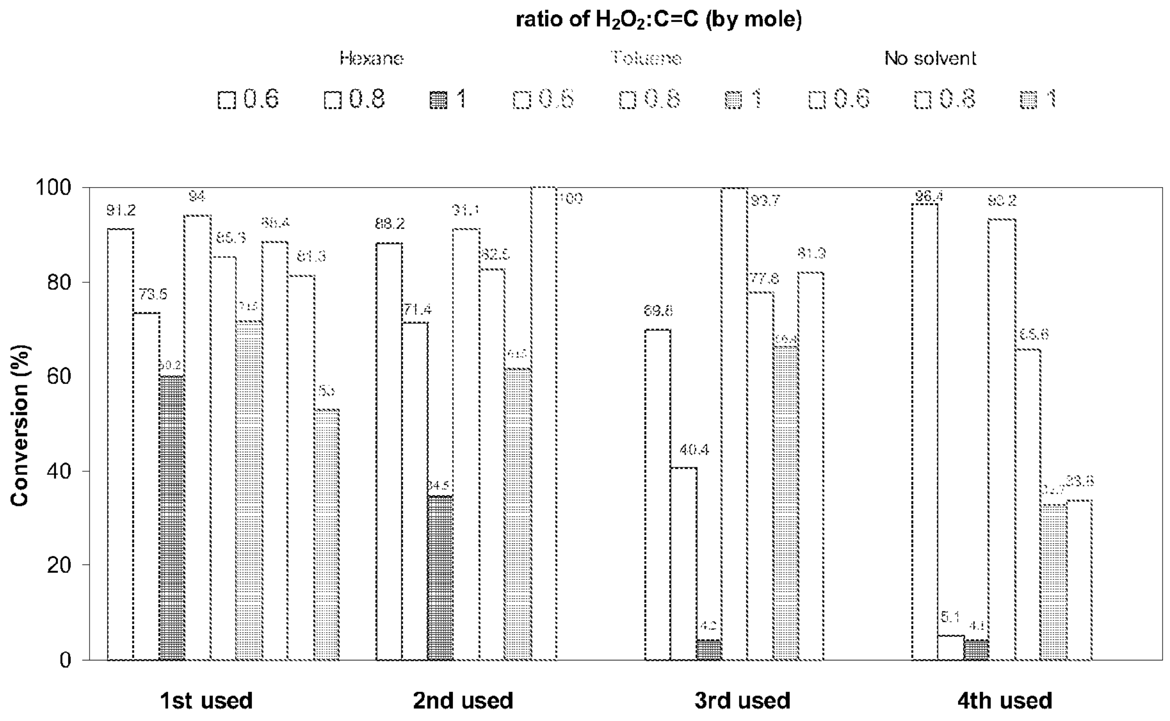

FIG. 6 presents the effects of organic solvent and hydrogen peroxide ($H_2O_2$) on chemo-enzymatic epoxidation of soybean oil triglyceride by NOVOZYME 435®.

Figure 7:
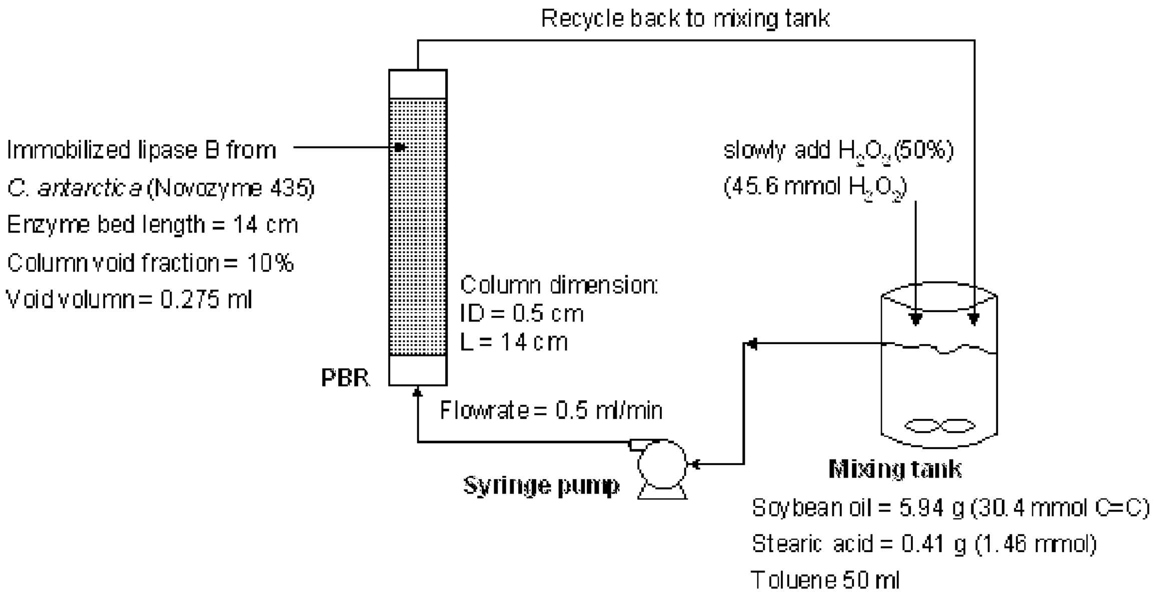

FIG. 7 diagrams the packed-bed reactor of chemo-enzymatic epoxidation to produce epoxy soybean oil triglyceride.

DESCRIPTION OF PREFERRED EMBODIMENTS

A process for converting unsaturated vegetable oils into polyols is comprised of one or more of the following conversion mechanisms: 1) bodying the vegetable oil to allow for increased hydroxyl equivalent weights, 2) partially oxidizing carbon-carbon π-bonds to attach reactive moieties such as epoxy or alcohol moieties, 3) reacting carbon-carbon π-bonds with monomers containing oxygen moieties, and 4) hydrolyzing ester bonds to replace ester moieties with alcohol moieties. A urethane foam recipe containing both alcohols and epoxies was effective with the polyols of this invention. The useful molecules of this invention are not limited to polyols and applications generally include those applications where alcohols of carbon numbers greater than about 12 are applied.

An embodiment of this invention is a process for converting an unsaturated molecule containing at least six carbon atoms to a polyfunctional oxygenate prepolymer, comprising the steps of bodying the unsaturated molecule at a temperature between 40° to 350° C. for less than 48 hours to form an oligomer with a viscosity at least 20% greater than the viscosity of the unsaturated molecule in an environment where diatomic oxygen is substantially absent and reacting the oligomer with an oxygen containing molecule.

Bodied Oil With Monomer Addition of Moiety—A preferred embodiment of this invention is bodied soybean oil with which acetol is reacted to attach alcohol moieties.

In the broader sense, this embodiment is a process for converting an unsaturated molecule containing at least six carbon atoms to an alcohol, comprising the steps of: bodying the unsaturated molecule at temperature between 150° to 350° C. for less than 48 hours until the viscosity of the bodied product is at least 20% greater than the viscosity of the unsaturated molecule, and reacting carbon-carbon π-bonds remaining in the bodied product with a monomer containing an oxygen containing moiety. The bodying is performed in the absence of diatomic oxygen.

The unsaturated molecule is preferably an unsaturated triglyceride.

The monomer containing an oxygen-containing moiety is preferably at least one monomer from the group comprising acetol, allyl alcohol, glycerin, glycols, epichlorohydrin, and acrolein.

Acetol is preferably reacted at temperatures between about 180° to about 250° C., and most-preferred reaction conditions are temperatures between about 195° to about 225° C. for 0.2 to 6 hours at a pressure/volume to keep greater than about 80% of the acetol in a liquid phase where the reaction occurs. No catalyst is generally necessary. Lower temperatures, such as down to about 140° C., provide the reaction with acetol at the expense of longer reaction times. Use of heterogeneous catalysts is an option. It is to be noted that while acetol reacts at these conditions, bodying of soybean oil with or without simultaneous reaction with acetol is preferably at temperatures between about 160° to about 280° C., and more preferably, between about 200° to about 240° C.

The pressure of the reaction is preferably maintained above the bubble point of the reaction mixture, which is largely determined by the concentration of the most volatile component. Typically, the monomers are present at a concentration between about 5% and about 20%. Pressures of 3 to 30 bars are generally adequate to maintain these monomer concentrations in solution.

A semibatch process is preferred to lessen vapor pressures. Generally, all glyceride reagents are loaded at zero reaction time and the monomers are added stepwise or continuously during reaction. Such an approach also applies to batch and continuous (such as a flow reactor designed to approach plug flow behavior) processes.

The bodying reaction may also be performed in the presence of a cross-linking monomer. Preferably, the cross-linking monomer is at least one cross-linking monomer from the group comprising dicyclopentadiene and divinylbenzene. The monomer addition step may be performed after the bodying step, or in the same reactor and at the same time as the bodying step. The monomer and the cross-linker are preferably present at a concentration between about 2% and about 20%, and more preferably, between about 8% and about 16%.

Allyl alcohol preferably is reacted with the bodied product at a temperature between about 240° to about 340° C. More preferred reaction conditions for reaction with allyl alcohol include a reaction temperature between about 250° to about 310° C.

Glycerol and glycols such as ethylene glycol will react with bodied ester products to attach alcohol moieties, without being bound by any particular theory or mechanism, by at least two mechanisms. First, carboxylic acid moieties on the bodied product will esterify with the alcohols on the glycerol or glycol. Second, ester moieties in the bodied product will transesterify with the alcohols. In the presence of base catalysts, transesterification will occur at ambient temperatures, but more preferably at temperatures above about 50° C. Preferred reaction temperatures for glycerol and glycol addition are between about 50° and about 340° C. At temperatures above 230° C., glycerol may undergo side-reactions, and so, preferred temperatures are below about 230° C. The more-preferred temperatures are between about 150° and about 230° C. because in this temperature range the reaction proceeds without catalysts. Reaction times from 30 minutes to 3 hours are typical for these esterification and transesterification reactions, and these times will vary based on mixing, viscosity of mixture, and the alcohol.

Glycerol and glycols may react with the unsaturated molecule containing at least six carbon atoms at the same time the bodying reaction occurs or after the bodying reaction occurs. Reaction after the bodying reaction may be conducted at lower temperatures with advantages associated with reduced degradation of the glycerol and glycols. Mixing may be utilized to promote the esterifications and transesterifications since glycerol and glycols tend to form immiscible phases with soybean oil and bodied products. Use of heterogeneous catalysts is preferred for the transesterification reactions. Suitable catalysts include solid acid catalysts, solid basic catalysts, and nickel-containing catalysts.

Preferably, the bodied product with the attached oxygen-containing moiety is formed under process conditions that result in an acid number less than 30 and a hydroxyl number greater than 20. Excess acidity (i.e., greater than about 10) is preferably neutralized as described in the section on epoxy neutralization of residual acidity.

Bodying and monomer addition reactions may be enhanced with catalysts. Preferably, the catalyst is at least one catalyst from the anthracene derivatives group including anthraquinone (i.e., 9,10-dioxoanthracene) and other organic catalysts with at least one ketone moiety and at least one carbon-carbon π-bond moiety. The catalyst is preferably a solid at temperatures below about 100° C. The catalyst may be present at a concentration between about 0% and about 10% (wt), and preferably between, about 1% and about 5%. The catalyst is preferably a solid at temperatures less than about 100° C., such that it may be readily filtered from the liquid bodied product for recycling.

The bodied product with the attached oxygen-containing moiety is preferably further reacted with an isocyanate to form a urethane polymer.

Temperatures higher than about 350° C. may be used to produce bodied soybean oil prior to addition of monomers. An iodine number of 105 was obtained in a flow reactor at 370° C. feed with refined soybean oil with a residence time of 82 minutes; however, the acid number was 33. By comparison, an iodine number of 101 was obtained in a flow reactor at 350° C. feed with refined soybean oil with a residence time of 93 minutes with an acid number of 22. Generally speaking, higher temperatures lead to greater acidity and poorer product. Temperatures up to about 390° C. will work to produce bodied soybean oil, but the oil is not as good of quality as that produced at lower temperatures.

Epoxy Neutralization of Residual Acidity—This product, or one of many products of these embodiments having an acidity greater than 10, is preferably reacted with an epoxy-containing molecule to reduce the acid number. A product having an attached oxygen-containing moiety and an acid number greater than 20 is preferably reacted with an epoxy-containing molecule to reduce the acid number to a value less than 15. The epoxy-containing molecule is preferably epoxy soybean oil (i.e., epoxidized soybean oil, ESBO), and the reaction with epoxy soybean oil is preferably at a temperature between 140° and 190° C. without any additional catalyst. Typically, the epoxy soybean oil is applied at concentrations between about 1% and about 20% (wt). It has been shown that 20% works to neutralize an acid number of 50. The reaction time is preferably between about 2 and 17 hours, with times less than about 9 hours being desirable. The more preferred reaction conditions are 170° C. for 6 to 8 hours. The use of ESBO can lead to cross-linking, increased molecular weights of the polyol, and higher viscosities. Other epoxy compounds such as butylene oxide, propylene oxide, and ethylene oxide will neutralize the acid without the crosslinking and without significant increases in viscosity.

EXAMPLES

The following examples demonstrate preferred embodiments of the invention. They shall be interpreted are illustrative and not in a limiting sense.

Example 1

Reaction of Bodied Soybean Oil with Allyl Alcohol or Acetol—Reactions of bodied soybean oil were conducted in sealed containers in an oven without agitation. The bodied soybean oil (BSBO) was prepared by maintaining refined soybean oil at 330° C. for 30 minutes—a notable increase in viscosity indicated that oligomerization occurred in this bodying process. Iodine values were followed where a decrease in iodine values indicated that carbon-carbon π-bonds reacted.

The iodine number of soybean oil was 134. The BSBO had an iodine number of 97. Table 1 summarizes the results for the reaction of allyl alcohol with BSBO. In the course of these reactions at varying loadings of allyl alcohol, the iodine value of soybean oil decreased from 97 to 65-68. Exp. #4 and #5 of Table 1 show that soybean oil also reacted directly with allyl alcohol.

TABLE 1

Reaction of bodied soybean oil (BSBO) and soybean oil (SBO) with allyl alcohol.

| Exp. # | Oil (g) | Allyl Alcohol (g) | Allyl Alcohol (wt %) | T (° C.) | Duration (h) | Iodine Value |
|---|---|---|---|---|---|---|
| 1 | 6.02 (BSBO) | 0.74 | 12.3 | 300 | 2 | 68 |
| 2 | 6.03 (BSBO) | 0.35 | 5.8 | 300 | 2 | 66 |
| 3 | 6.02 (BSBO) | 1.10 | 18.3 | 300 | 2 | 65 |
| 4 | 6 (SBO) | 0.9 | 15 | 300 | 2 | 100 |
| 5 | 6 (SBO) | 0 | 0 | 300 | 2 | 118 |

The iodine value of soybean oil was 134.
The iodine value of soybean oil bodied for 30 minutes at a temperature of 330° C. (BSBO) was 97.

Table 2 summarizes the results for the reaction of acetol with BSBO or SBO. In the course of these reactions at varying loadings of acetol the iodine value of BSBO decreased from 97 to 63-65. Exp. #4 of Table 2 shows that soybean oil also reacted directly with acetol.

These results indicate that both allyl alcohol and acetol reacted with the carbon-carbon π-bonds of BSBO and presumably attached to the oil, leading to polyols having primary alcohols. To confirm that the decreases in iodine numbers were not simply the further oligomerization of BSBO with other BSBO, a control was performed using glycerin.

TABLE 2

Reaction of BSBO with acetol.

| Exp. # | BSBO (g) | Acetol (g) | Acetol (wt %) | T (° C.) | Duration (h) | Iodine Value |
|---|---|---|---|---|---|---|
| 1 | 6.03 | 1.39 | 23 | 180 | 9 | 65.9 |
| 2 | 6.05 | 0.91 | 15 | 180 | 9 | 65.2 |
| 3 | 6.00 | 0.45 | 7.5 | 180 | 9 | 63.1 |
| 4 | 6.00 (SBO) | 1.39 | 23 | 180 | 9 | 95 |

Table 3 summarizes the results for the reaction of glycerin with BSBO. In the course of these reactions at varying loadings of glycerin the iodine value of BSBO remained at 97. The results of the glycerin reaction indicate that glycerin did not interact with the carbon-carbon π-bonds and is further indication that both allyl alcohol and acetol reacted with the carbon-carbon π-bonds.

TABLE 3

Reaction of BSBO with glycerin.

| Exp. # | BSBO (g) | Glycerol (g) | Glycerol (wt %) | T (° C.) | Duration (h) | Iodine Value |
|---|---|---|---|---|---|---|
| 1 | 6.02 | 0.74 | 12.3 | 210 | 9 | 96 |
| 3 | 6.0 | 1.12 | 18.7 | 210 | 9 | 98 |

In the case of ally alcohol and acetol reactions, a series of screening reactions were conducted to identify conditions that led to the desired interaction. Higher temperatures were required for good allyl alcohol reaction than for acetol reaction. The lower threshold temperature for good acetol reaction is indicative of observations that acetol tends to polymerize at temperatures near 200° C. (Dasari et al., Appl. Catal. A (2005) 281(1-2):225-231).

In the interpretation of these data it was assumed that if glycerin did not react with the carbon-carbon bonds π-bonds at 210° C., that it would also not react at 180° C.

FTIR analysis was performed in addition to the iodine value tests to determine if alcohol was present in the products of these reactions. In each case, the products were washed several times with water and dried. Any free alcohol should be readily removed through these washing steps. In addition, the self-polymerization products of both allyl alcohol and acetol are water-soluble and would also be removed in the water washes. Therefore, any alcohol moiety that shows up in the FTIR would be indicative of alcohols attached to the BSBO.

In the FTIR spectrum of the BSBO control for these studies the absence of a transmittance peak at the 3470/cm wavelength indicated that no alcohol moieties were present on the BSBO. FTIR product spectra indicate that alcohol moieties were present on BSBO for both the allyl alcohol and the acetol reaction products.

These preliminary results indicate that soy-based polyols may be prepared with the following advantages:

A single-pot reactor approach that should have processing costs less than $0.15 per pound, as of the filing date of this patent.

Ample and good degrees of freedom to control the average number of alcohols per molecule and the average hydroxyl equivalent weight.

The ability to create primary alcohol moieties.

FIG. 1 summarizes the performance of several synthesized and commercial soy-based polyols. A product based on reacting an acetol monomer with soybean oil is one of only two formulations that out-performed the petroleum-based commercial polyol (Voranol 490) used as a control.

These results demonstrate the great potential for using acetol as a monomer for converting soybean oil to polyols in a very simple process.

Example 2

Simultaneous Bodying With Reaction Addition

This example illustrates a single-step reaction for the simultaneous bodying of the soybean oil and the reactive addition of acetol. The effects of anthraquinone as a catalyst and dicyclopentadiene as a crosslinker were also evaluated. The following abbreviations are used in Tables 4 and 5: soybean oil (SBO), dicyclopentadiene (DCP), anthraquinone (AQ). These reactions were conduced in a Par reactor or in small steel vessels.

TABLE 4

Summary of Parr reactor studies on simultaneous bodying and reaction addition.

| RXN # | SBO (g) | Acetol (g) | DCP (g) | AQ (g) | T (° C.) | Time (hr) | Acid No. | Iodine No. | OH No. |
|---|---|---|---|---|---|---|---|---|---|
| 1 | 100 | 15 | 0 | 2.5 | 250 | 20 | 24 | 95 | 52 |
| 2 | 100 | 15 | 0 | 2.5 | 250 | 20 | 25 | 92 | 55 |
| 5 | 100 | 15 | 14 | 0* | 250 | 20 | 46 | 106 | 72 |
| 6 | 100 | 15 | 14 | 0* | 250 | 20 | 45 | 100 | 72 |
| 7 | 100 | 15 | 14 | 2.5 | 250 | 20 | 39 | 99 | 52 |
| 8 | 100 | 15 | 14 | 5 | 250 | 20 | 54 | 98 | 60 |

*viscosity was low indicating lack of bodying reaction

TABLE 5

Summary of steel vessel reactor studies on simultaneous bodying and reaction addition.

| RXN #. | SBO (g) | Acetol (g) | DCP (g) | AQ (g) | Acid No. | Iodine No. | OH No. |
|---|---|---|---|---|---|---|---|
| v7 | 100 | 15 | 0 | 2.5 | 72.3 | 88.3 | 62 |
| v8 | 100 | 15 | 0 | 2.5 | 67.5 | 92.6 | 61 |
| v9 | 100 | 15 | 14 | 0* | 54.0 | 91.0 | 74 |
| v10 | 100 | 15 | 14 | 0* | 48.0 | 105.7 | 67 |
| v11 | 100 | 15 | 14 | 2.5 | 49.7 | 100.1 | 70 |
| v12 | 100 | 15 | 14 | 2.5 | 47.8 | 98.9 | 74 |
| v13 | 100 | 15 | 14 | 2.5 | 48.1 | 100.1 | 81 |
| v14 | 100 | 15 | 14 | 2.5 | 47.1 | 100.4 | 80 |

*viscosity was low indicating lack of bodying reaction.

Several conclusions can be drawn from these reactions. Anthraquinone increased the viscosity as a result of this processing (observation not recorded in the tables) and it was recoverable as a filterable solid after the reaction. Therefore, it acted as a bodying catalyst that allowing bodying at temperatures of about 240-250° C., whereas temperatures >300° C. are normally needed for this effect. Concentrations of anthraquinone greater than 2.5% did not significantly promote a faster reaction. Bodying at lower temperatures resulted in a product with less darkening. Acetol provided for increased hydroxyl (OH) numbers. The presence of dicyclopentadiene led to higher acid and OH numbers possibly due to the abundance of conjugated carbon-carbon π-bonds that allowed for more abundant acetol addition.

For all of these reactions, the iodine number decreased from 36% to 46% (note that acetol in the initial reaction mixture caused an increase of initial iodine numbers to values between 130 and 145) indicating that the carbon-carbon π-bonds reacted. At least part of these reactions occurred between the acetol and the oil, leading to the attachment of the acetol and desired alcohol functionality. This was further substantiated by the increase in OH numbers above and beyond the increase in acid numbers. For the reactions without the anthraquinone, the reduction in iodine numbers was less (36-39% versus 41-46%), indicating that the anthraquinone catalyzed the bodying process. This was further substantiated by the observed higher viscosity of solutions with this catalyst. It is hypothesized that the acetol attachment increased the acidity, and that the increased acidity was not solely due to hydrolysis side-reactions.

Partially Hydrolyzed Bodied Soybean Oil—An alternative embodiment of this invention is a B-side monomer of a urethane formulation prepared by partially hydrolyzing bodied soybean oil.

In the broader sense, this embodiment is a process for synthesizing a B-side monomer of a urethane formulation comprised of the following: bodying an unsaturated glyceride to form a bodied glyceride, hydrolyzing some of the ester bonds of the bodied glyceride to form alcohol moieties on the glyceride and a free fatty acid and separating the free fatty acid from the B-side monomer containing alcohol moieties. Water is typically needed to promote hydrolysis, preferably from about 0.5% to about 10%, and most preferably, about 5%. Use of a surfactant is preferred since it promotes faster hydrolysis.

Preferably, the hydrolysis is selective hydrolysis performed in a manner to selectively remove saturated fatty acids from the glyceride. Preferably, the hydrolysis is selective hydrolysis performed by an enzymatic reaction at a temperature between about 30° and 50° C. in a phosphate buffer solution in a manner to selectively remove saturated fatty acids from the glyceride. Preferably, the partially hydrolyzed bodied glyceride has a hydroxyl number greater than 20 and is reacted with an epoxy-containing molecule to reduce the acid number. Typically, the partially hydrolyzed bodied glyceride has an acid number greater than 10 and a hydroxyl number greater than 20 and is reacted with an epoxy-containing molecule to reduce the acid number. Longer hydrolysis times lead to greater acidity and hydroxyl numbers—these times are highly dependent on the enzyme and state (i.e., free versus immobilized) of the enzyme. The preferred means to handle high acidity is through neutralization with epoxy as described earlier in the section entitled Epoxy Neutralization of Residual Acidity.

Hydrolysis was effectively performed using a packed-bed of immobilized enzyme. The enzyme loading was such that 10 minutes of flow created a mass of bodied product equal to the mass of immobilized enzyme where the bodied product reached 15% hydrolysis. The enzyme was a lipase from *Burkholderia cepacia*. Free enzyme concentrations are typically less than about 0.5% with lower loadings having slower reaction times. When performing the reaction in a stirred tank, typical reaction times are between 1 and 48 hours.

Example 3

Hydrolysis of Bodied Soybean Oil

This example illustrates the enzymatic hydrolysis of bodied soybean oil to form a polyol. The reagents included lipases from *Candida rugosa* (Lipase AY "Amano"), *Burkholderia cepacia* (Lipase PS "Amano"), *Penicillium roquefortii* (Lipase R "Amano"), *Aspergillus niger* (Lipase A "Amano"), and *Mucor javanicus* (Lipase M "Amano") from Amano Enzyme USA (Elgin, Ill., USA) and a lipase from *Rhizomucor miehei* from Sigma-Aldrich (St. Louis, Mo., USA) as well as food-grade refined soybean oil from a local grocery store.

Bodied soybean oil was produced by heating soybean oil at 330° C. for 45 min under a nitrogen gas environment. The heating process was done in a 1-liter Parr reactor and the volatile matters were removed during the reaction with a nitrogen purge. After 45 min, the viscosity of the oil was increased by 23% and the iodine number was reduced by 45%; the viscosity and iodine values for the bodied soybean oil were 0.67 $cm^2s^{-1}$ and 80, respectively. Molecular weight distribution was determined by GPC.

The bodied soybean oil was partially hydrolyzed by commercial lipases without any surfactant or organic solvent. Bodied soybean oil (15 g), phosphate buffer at pH 7.0 (15 g) and lipase (70 mg) were placed in a 125-ml flask and the reaction conditions were controlled by an incubator shaker (Psycrotherm, New Brunswick, N.J., USA) at 45° C. and 300 rpm. Triplicate samples and one control sample (substrate+buffer, and without enzyme) were carried out concurrently.

Three reaction times were used: 1.5, 3, and 24 h. After the desired reaction times, the reaction products were left at room temperature to cool, and then washed and analyzed. The reaction conditions produced 15% to 50% of hydrolysis and the isolated polyols were typically about 50% by weight of the bodied soybean oil.

After the reaction, 45 ml of $Na_2CO_3$ (0.5 M) and 90 ml of diethyl ether were mixed together with the reaction product in a separatory funnel. The mixture was left overnight before high speed centrifuge was applied to help separate the fatty acid soap from the ether phase. Ester glycerides were in the ether phase (upper portion), whereas liberated fatty acids (free fatty acid soaps) were in the water phase (lower portion). Free fatty acids were recovered by acidification with HCl (conc.) and then solvent extraction by diethyl ether. Finally, diethyl ether in both the ether glycerides and hydrolyzed fatty acids was removed at 50° C. in an oven. Washing studies were also performed with the polyol product and $NaHCO_3$ (aqueous 0.5 M, pH 8.0).

The percent of hydrolysis (Table 6) is defined by the acid number of the hydrolyzed product. Acid enrichment numbers (AEN) of saturated fatty acids in the acid residue phase were calculated and reported in Table 6. An acid enrichment number of 1 or greater indicates that the enzyme significantly hydrolyzed the saturated fatty acids.

The hydroxy (OH) numbers reported in Table 6 were equal to the acid number of the hydrolyzed product (before product workup) because one mole of hydroxy is formed when one mole of acid is hydrolyzed. The hydroxy numbers of a few of the polyol products were determined using the standard method of hydroxy number titration (ASTM D4274, 2005).

The reported hydroxy numbers in Table 6 were comparable to the numbers from the titration method.

TABLE 6

Hydrolysis (%) and acid enrichment numbers of saturated fatty acids in the acid residue phase after the hydrolysis of bodied soybean oil.

| | | 1.5 h/3 h/24 h | | |
|---|---|---|---|---|
| Enzyme | | AEN | Hydrolysis (%) | OH-number (mgKOH/g) |
| *C. rugosa* | (C16:0) | 1.6 ± 0.1/1.4 ± 0.2/ 1.3 ± 0.2 | 22/27/42 | ~42/~51/~80 |
| | (C18:0) | 1.1 ± 0.1/0.9 ± 0.1/ 0.9 ± 0.1 — | | |
| *B. cepacia* | (C16:0) | 1.1 ± <0.1/1.2 ± 0.1/ 1.2 ± 0.1 | 24/35/44 | ~46/~67/~84 |
| | (C18:0) | 1.0 ± <0.1/1.1 ± 0.1/ 1.1 ± 0.1 — | | |
| *A. niger* | (C16:0) | 1.2 ± <0.1/1.1 ± 0.1/ 1.0 ± 0.1 | 15/15/23 | ~29/~29/~44 |
| | (C18:0) | 1.1 ± <0.1/1.0 ± 0.1/ 1.0 ± 0.1 — | | |
| *M. javanicus* | (C16:0) | 1.1 ± 0.1/1.1 ± 0.1/ 1.1 ± <0.1 | 17/21/43 | ~32/~40/~82 |
| | (C18:0) | 1.0 ± 0.1/1.1 ± 0.1/ 1.0 ± <0.1 — | | |
| *R. miehei* | (C16:0) | —/1.1 ± 0.1/1.1 ± 0.1 | —/29/39 | —/~55/~74 |
| | (C18:0) | —/1.0 ± <0.1/1.1 ± 0.1 — | | |

Two reactions were performed to hydrolyze bodied soybean oil with enzyme from *C. rugosa* (1.8 mg enzyme/gram oil). After the reaction reached 40% hydrolysis (acid number about 76 mg KOH/g), the products were washed with different base solutions; $Na_2CO_3$ (0.5 M, pH 11.0) and $NaHCO_3$ (0.5 M, pH 8.0), to remove fatty acids. The pH11 solution wash reduced the acid number of the oil to 10, while the pH 9 solution only reduced the acid number to 75.

This embodiment including the steps of bodying and reacting with a monomer containing an oxygen-containing moiety preferably produces a B-side molecule capable of reacting with A-side monomers to form a polyurethane. The preferred B-side molecule has the following properties: an average of at least 1.5 oxygen ester bonds per molecule but less than 8 oxygen bonds per molecule, a viscosity between 500 and 12,000 centapoise at 25° C. (more preferably between 500 and 4,000 centapoise), reactivity with Karl-Fisher reagent indicating a hydroxyl number between 30 and 200 (more preferably between 40 and 150), and a chemical analysis spectrum indicating the presence of 5-ring moieties indicating a Diels-Alder formation mechanism.

Vegetable Oil with Monomer Addition of Moiety—An alternative embodiment of this invention is soybean oil with which acetol is reacted to attach alcohol moieties. In the broader sense, this embodiment is a process for converting an unsaturated molecule containing at least six carbon atoms to an alcohol, comprising the steps of: reacting carbon-carbon π-bonds of the unsaturated molecule with a monomer containing an oxygen-containing moiety at a temperature between about 150° to about 350° C. for less than 48 hours to form an oxygen-containing product.

The unsaturated molecule is preferably an unsaturated triglyceride. The monomer containing an oxygen-containing moiety is preferably at least one monomer from the group comprising acetol, allyl alcohol, glycerin, glycols, epichlorohydrin, and acrolein.

Acetol is preferably reacted at temperatures between about 180° to about 250° C., and most-preferred reaction conditions are temperatures between about 195° to about 225° C. for 0.2 to 6 hours at a pressure/volume to keep greater than about 80% of the acetol in a liquid phase during the reaction. No catalyst is generally necessary. Use of a heterogeneous catalyst is a good option.

Allyl alcohol preferably is reacted with the bodied product at a temperature between about 240° to about 340° C. More preferred reaction conditions for reaction with allyl alcohol include a reaction temperature between about 250° to about 310° C.

The addition of monomers at these temperatures can increase acidity, often resulting in acid numbers greater than 10 and a hydroxyl number greater than 20. The product is generally reacted with an epoxy-containing molecule to reduce the acid number. The preferred means to handle high acidity is through neutralization with epoxy, as described earlier in the section entitled Epoxy Neutralization of Residual Acidity. When a multi-functional epoxy compound is used, both the hydroxyl number and molecular weight of the product can increase.

The oxygen-containing product is further preferably reacted with an isocyanate to form a urethane polymer.

Example 4

Acetol Addition to Soybean Oil

Acetol was reacted with soybean oil in small, closed steel reactors at the temperatures and times indicated in Table 7. The hydroxyl number increased as indicated for the reaction product after washing with water. The iodine values were between 132 and 118 cg Iodine/g as compared to an initial value of 132 for soybean oil. The acid values fluctuated from 10 to 25 in the product of low concentrations of acetol (7% to 10% per samples 1 to 10) and from 40 to 58 mgKOH/g at higher acetol concentrations. These data illustrate the successful addition of acetol to soybean oil. Evidence suggests that acetol reacts with conjugate carbon-carbon π-bonds in soybean oil. Reaction times of more than 9 hrs provided good results (as well as the times indicated in Table 7).

TABLE 7

Results for reaction addition of acetol to soybean oil.

| No. | Reaction | Temp (° C.) | Time (h) | OH number |
|---|---|---|---|---|
| 1 | SBO + Acetol (7%) | 180 | 13 | 15 |
| 2 | SBO + Acetol (10%) | 160 | 36 | 23.9 |
| 3 | SBO + Acetol (10%) | 170 | 20 | 21.2 |
| 4 | SBO + Acetol (10%) | 158 | 16 | 23.3 |
| 5 | SBO + Acetol (10%) | 170 | 18 | 24.4 |
| 6 | SBO + Acetol (10%) | 165 | 24 | 38.3 |
| 7 | SBO + Acetol (10%) | 180 | 16 | 47.3 |
| 8 | SBO + Acetol (10%) | 190 | 16 | 39.9 |
| 9 | SBO + Acetol (14%) | 190 | 28 | 34.0 |
| 10 | SBO + Acetol (10%) | 180 | 24 | 44.7 |
| 11 | SBO + Acetol (20%) | 160 | 48 | 21.7 |
| 12 | SBO + Acetol (15%) | 185 | 48 | 39.9 |
| 13 | SBO + Acetol (15%) | 185 | 96 | 37.1 |
| 14 | SBO + Acetol (15%) | 190 | 48 | 44.2 |
| 15 | SBO + Acetol (15%) | 190 | 72 | 37.4 |
| 16 | SBO + Acetol (15%) | 220 | 24 | 69.2 |
| 17 | SBO + Acetol (15%) | 220 | 72 | 60.7 |
| 18 | SBO + Acetol (15%) | 240 | 24 | 44.5 |
| 19 | SBO + Acetol (15%) | 240 | 48 | 55.3 |
| 20 | SBO + Acetol (20%) | 220 | 24 | 64.4 |

B-Side Monomer of Urethane Formulation—Monomer Containing Both Epoxy and Alcohol—An alternative embodiment of this invention is a monomer urethane formulation where the monomer has both alcohol and epoxy moieties.

In the broader sense, this embodiment is an B-side monomer of a urethane formulation comprised of the following: a molecular structure containing at least 30 carbon atoms, at least one alcohol moiety, and at least one epoxy moiety. Preferably, the molar ratio of epoxy to hydroxyl moieties in the formulation (before reaction) is greater than 1:4, more preferably greater than 1:3 and less than 1:0.5, and most preferably, between 1:2.8 and 1:1.

Preferably, the monomer is a glyceride and the epoxy moiety is a secondary epoxy moiety on a fatty acid containing at least 16 carbon atoms.

Preferably, the glyceride is a diglyceride. Preferably the glyceride is an oligomer of at least two glycerides.

The most-preferred embodiment of this invention is a mixture of soybean oil that is epoxidized to form epoxy soybean oil and a polyol having a functionality greater than 3 and molecular weight greater than 500.

Diglyceride Formed from Selective Hydrolysis of Epoxy Soybean Oil—An alternative embodiment of this invention is a B-side monomer of a urethane formulation containing the diglyceride formed by the selective hydrolysis of epoxy soybean oil.

In the broader sense, this embodiment is a process for synthesizing a B-side monomer of a urethane formulation comprised of the following: hydrolyzing some of the ester bonds of a glyceride-containing material to form alcohol moieties on the glyceride and a free fatty acid, and separating the free fatty acid from the B-side monomer containing the alcohol moieties that react with isocyanates.

Preferably, the hydrolysis is selective hydrolysis performed in a manner to selectively remove saturated fatty acids from the glyceride.

Preferably, the glyceride-containing material is from the group comprised of castor oil or epoxy soybean oil. While this embodiment has been described as a B-side monomer, the use of this diglyceride in a urethane formulation may be other than as a B-side monomer.

Urethane Formulation with a B-Side that is a Monomer Containing Both Epoxy and Hydroxyl Moieties—An alternative embodiment of this invention is a urethane formulation with a B-side that includes a monomer containing both hydroxyl and epoxy moieties.

In the broader sense, this embodiment is a urethane foaming process comprised of the following: an A-side monomer comprised of isocyanate molecules, a B-side monomer comprised of at least one monomer containing at least one epoxy moiety and at least one alcohol moiety, and at least one catalyst and at least one surfactant. The A-side, the B-side, the catalyst, and the surfactant form a PUF formulation that reacts to form a foam. Preferably, the molar ratio of epoxy to hydroxyl moieties in the formulation (before reaction) is greater than 1:4, more preferably greater than 1:3 and less than 1:0.5, and most preferably, between 1:2.8 and 1:1.

The catalyst (e.g., a liquid tertiary amine) serves to speed up the reaction of isocyanate and polyols. It is a crosslinking agent that forms a covalent bond in the polyurethane foam matrix. The function of the surfactant is to aid in the foam-forming processes and to avoid foam collapse and foam splitting.

Preferably, the monomer containing at least one epoxy moiety and at least one alcohol moiety is the diglyceride of epoxy soybean oil. Optionally, the hydrolysis uses enzymes that selectively remove the saturated fatty acid groups from the epoxy soybean oil. Preferably, the monomer containing at least one epoxy moiety and at least one alcohol moiety comprises from about 10% to about 50% of the B-side monomer mixture. Preferably, the PUF formulation contains 3% water in the B-side monomer mixture, and the isocyanate loading provides an isocyanate index between 100 and 130.

Example 5

Soy-Based Polyols from Selective Hydrolysis

This example provides experimental results for the selective hydrolysis of soybean oil. Chemicals/enzymes used for the example are lipases from *C. rugosa* (Lipase AY "Amano"), *B. cepacia* (Lipase PS "Amano"), *Pseudomonas* sp. (Cholesterol esterase, "Amano" 2), *P. roquefortii* (Lipase R "Amano"), *P. camembertii* (Lipase G "Amano"), *A. niger* (Lipase A "Amano"), *M. javanicus* (Lipase M "Amano"), immobilized lipase from *B. cepacia* that were purchased from Amano Enzyme USA, Elgin, Ill.; lipase from *R. miehei* purchased from Sigma-Aldrich, St. Louis, Mo.; epoxy soybean oil (VIKOFLEX7170) purchased from ATOFINA Chemicals Inc, Philadelphia, Pa.; refined soybean oil (Food Club brand vegetable oil) from a local grocery store; Diozald, Tetramethylammonium Hydroxide (TMAH, 25% in methanol), Oleic acid (90%), Linolenic acid (99%), Hydrogen Peroxide and Novozyme 435® (lipase B from *Candida antarctica*) from Sigma Aldrich, St. Louis, Mo.; linoleic acid (90%) purchased from City Chemical LLC, West Heaven, Conn.; flax seed oil from Jedwards International, Inc., Quincy, Mass.; and methanol, Diethyl ether, Potassium bicarbonate and Sulfuric acid from Fisher, Houston, Tex.

Hydrolysis of Soybean Oil and Epoxy Soybean Oil

The enzymes obtained from Amano Enzyme Inc. were studied at their optimum pH and temperature as recommended in the product specification sheets and the reactions with *R. miehei* lipase were conducted at 45° C. and pH 7.0. Table 8 shows operating conditions, and enzyme activity as reported from the enzyme suppliers.

Two grams of soybean oil or epoxy soybean oil and two grams of buffer solution were mixed in a 125-mL Erlenmeyer flask. The reactions were performed in a controlled environment incubator shaker (PSYCROTHERM, New Brunswick, N.J.) at the speed of 300 rpm. For a reaction at given pH, temperature and time, three replications and one control (substrate+buffer, and without enzyme) were carried out concurrently. The enzyme unit was 67.5 units per gram of substrate. The reaction was stopped by adding 20 mL of a mixture of methanol and diethyl ether (80:20).

TABLE 8

Operating pH and temperature for enzyme hydrolysis screening test.

| Lipase | pH | Temperature (° C.) | Activity, (units/gram) |
|---|---|---|---|
| *C. rugosa* | 7.0 | 45 | ≧30,000 |
| *B. cepacia* | 7.0 | 50 | ≧30,000 |
| *Pseudomonas* sp. | 7.0 | 35 | ≧10,000 |
| *P. camembertii* | 5.0 | 30 | ≧50,000 |
| *P. roquefortii* | 7.0 | 40 | ≧10,000 |
| *A. niger* | 6.0 | 45 | 12,000-15,000 |
| *M. javanicus* | 7.0 | 40 | ≧10,000 |
| *R. miehei* | 7.0 | 45 | ≧20,000 |

Only in the limit of zero hydrolysis will the true, fundamental selectivity of the hydrolysis be revealed in a single concentration profile. Conversion data at 100% hydrolysis will not reveal information on selectivity. Reaction times of this investigation were selected to provide about 15% conversion since soybean oil contains about 15% saturated fatty acids. The actual conversions are presented in FIG. 2 and typically varied from 5% to 20%.

After stopping the reaction, 80 mL of 0.5 M potassium bicarbonate and 15 mL of diethyl ether were added into the reaction product (glyceride-fatty acid mixtures). The mixture was placed in a separatory funnel. The glyceride portion (oil phase) was separated from the free fatty acid soap, which was in the lower water phase. Free fatty acid soap residues were recovered from the water phase by acidification with sulfuric acid and then by solvent extraction with diethyl ether. Lastly, the diethyl ether in both the glyceride fraction and acid residue fraction was evaporated at 45° C.

FIG. 2 presents the hydrolysis conversions and the compositions of the glyceride phase and the fatty acid phase after enzyme hydrolysis of soybean oil. FIG. 3 shows the hydrolysis conversions and the constituents in the glyceride phase and the fatty acid phase after enzyme hydrolysis of epoxy soybean oil.

After product workup, the enrichment number of each acyl moiety in the fatty acid phase was calculated in order to investigate enzyme selectivity. The following equation defines the enrichment number:

$$\text{Enrichment number of acyl moiety } 'A' \text{ in fatty acid residue} = \frac{(\%\text{ normalization of } 'A' \text{ in fatty acid phase})}{(\%\text{ normatization of } 'A' \text{ in triglyceride substrate})}$$

where A is palmitic acid, stearic acid, or other acyl moieties

The total of every component's signal is 100 in percent normalization.

The higher the acid enrichment number, the higher the enzyme selectivity toward hydrolyzing a particular acyl moiety. FIG. 2 and FIG. 3 show enrichment numbers from the reactions of soybean oil triglyceride and of epoxy soybean oil triglyceride, respectively.

Rates of hydrolysis significantly increased in the reaction of epoxy soybean oil relative to soybean oil (see FIG. 2 and FIG. 3). The reaction conversion increased from 25% to 37% (24 h) by *C. rugosa* lipase. The hydrolysis of epoxy soybean oil by *B. cepacia* lipase resulted in a 45% conversion (2 h) while the reaction with soybean oil yielded only 1% (2 h). This is likely due to the emulsifying characteristics of the epoxy group, which tends to increase the interface area between lipids and water.

The emulsifying nature of epoxy soybean oil was confirmed by observations. Lipid-water mixtures during and after the hydrolysis of epoxy soybean oil were cloudy, while mixtures with soybean oil were less cloudy and more-readily separated into isolatable phases.

Urethane Formulation with B-Side that is Mixture of Epoxy and Alcohol Monomers—An alternative embodiment of this invention is a urethane formulation with a B-side comprised of a mixture of an epoxy monomer and an alcohol monomer.

In the broader sense, this embodiment is a urethane foaming process comprised of the following: an A-side monomer comprised of isocyanate molecules, a B-side monomer mixture comprised of at least one monomer containing at least two epoxy moieties and at least one monomer containing at least two alcohol moieties, where the B-side contains at least 30% by weight of the monomer containing the alcohol moieties, at least one catalyst, at least one surfactant, and at least 20% by weight of the monomer containing the epoxy moieties. Stated differently, the molar ratio of epoxy to hydroxyl moieties in the formulation (before reaction) is greater than 1:4, more preferably, greater than 1:3 and less than 1:0.5, and most preferably, between 1:2.8 and 1:1. The A-side, B-side, catalyst, and surfactant form a PUF formulation that reacts to form a foam.

Preferably, the monomer containing at least two epoxy groups is epoxy soybean oil. Preferably, the monomer containing at least two epoxy groups comprises from 10% to 50% of the B-side monomer mixture. Preferably, the PUF formulation contains 3% water in the B-side monomer mixture, and the isocyanate loading provides an isocyanate index between 100 and 130.

Example 6

Rigid Foam with Epoxy in B-Side—Rigid polyurethane foams were made using a standard mixing procedure. This procedure involved intensive mixing using a commercial drill press (Colcord-Wright, St. Louis, Mo.) fitted with a 25.4 cm shaft with a 5 cm impeller arranged to turn at 3450 rpm. The B-side mixture components, which included polyether polyol (Voranol 490), soybean oil polyols, catalyst, surfactant, and water (as a blowing agent), as shown in Table 9, were sequentially weighed by a balance and added into a 0.946 L (1 quart) disposable paperboard container fitted with a steel frame with four baffles next to the container wall, and mixed at 3450 rpm for 10-15 s. Then stirring was stopped, to allow the mixture to degas. After 120 s, polymeric isocyanate, with an index of 110, was rapidly added and stirring was continued for another 10 s at the same speed. Finally, the reacting mixtures were poured immediately into wooden boxes (220 by 220 by 150 mm) and allowed to rise at ambient conditions. Foams were removed from boxes after 1 hour and allowed to cure at room temperature (23° C.) for one week before cutting into test specimens with a band saw. The properties of typical rigid polyurethane foams made from 50% polyether polyol and 50% soybean oil polyols are shown in Table 10.

TABLE 9

Composition of the B-side mixture.

| Materials | Parts |
|---|---|
| Voranol ® 490 | 90-50 |
| Soybean oil polyol | 10-50 |
| Water | 3 |
| Polycat ® 5 | 1.26 |
| Polycat ® 8 | 0.84 |
| Dabco ® DC 5357 | 2.5 |

TABLE 10

Properties of typical polyurethane foams using 100% polyether polyol or 50% polyether polyol and 50% soybean oil polyols.

| Polyols | Thermal conductivity (W/mK) | Density ($kg/m^3$) | Compressive strength (kpa) |
|---|---|---|---|
| 100% Voranol ® 490 | 0.02724 | 49.44 | 397.6 |
| 50% Voranol ® 490 50% Epoxidized and oxidized soybean oil | 0.02803 | 45.62 | 294.6 |
| 50% Voranol ® 490 50% Epoxidized bodied soybean oil | 0.02744 | 46.57 | 343.8 |
| 50% Voranol ® 490 50% Diglyceride of epoxy soybean oil | 0.02562 | 34.16 | 284.0 |

Addition Reaction to Epoxy SBO—An alternative embodiment is a process for synthesizing a polyol comprising an addition reaction whereby a carboxylic acid having a carbon number of at least 12 reacts with an epoxy of a glyceride to form alcohol and ester moieties at the carbons of the epoxy moiety and a hydrocarbon chain containing at least 12 carbons. Preferably, the carboxylic acid is a free fatty acid having a carbon number greater than 13, the epoxy is an epoxidized vegetable oil, and the mass ratio of epoxidized vegetable oil and fatty acid is between 2 and 1. More preferably, this ratio is between 2 and 1.4. The preferred reaction conditions are 170° C. for 6 to 8 hours. More generally, the reaction conditions are from 140° to 190° C. for 2 to 17 hours. An even more general temperature range is from 120° to 260° C.

Alternatively, the carboxylic acid is an estolide comprised of a chain of fatty acids having carbon numbers greater than 13 and the epoxy is an epoxidized vegetable oil. Yet another alternative is where the carboxylic acid is a hydrolyzed oligomer of a bodied vegetable oil.

The preferred epoxy is an epoxidized vegetable oil like epoxy soybean oil. Preferably, the addition reaction is carried out at a temperature between 140° to 190° C.

B-Side Monomer with Large Non-Functional Branch—An alternative embodiment is a B-side monomer of a urethane formulation comprised of a molecular structure containing at least 30 carbon atoms, at least one oxygen containing moiety, and at least one branch attached to a carbon containing the oxygen moiety, where the branch contains at least eleven carbon atoms, no oxygen containing moieties, and ends in a methyl carbon. The process for synthesizing this B-side monomer includes reacting a carboxylic acid with an epoxified glyceride, such as epoxy soybean oil. An example carboxylic acid is a free fatty acid such as linoleic acid. By example, linoleic acid will form a branch that is a straight-chain hydrocarbon branch. These monomers will react with isocyanates to form urethane polymers, where the branch of at least eleven carbons is a branch in the urethane polymer.

Example 7

Polyols Formed from Reaction Addition to Epoxy Soybean Oil—This example illustrates the synthesis of higher molecular weight polyols from addition reaction to epoxy soybean oil. Chemicals used in the synthesis include castor oil from Alnor Oil Company (Valley Stream, N.Y.), soybean oil (food grade) obtained from a local grocery store, epoxy soybean oil (Vikoflex® 7170) from Atofina Chemicals (Philadelphia, Pa.). Ricinoleic acid (technical grade) from Arro Corporation (Hodgkins, Ill.), enzyme *Candida rugosa* (lipase Amano "AYS") from Amano Enzyme Inc. USA (Elgin, Ill.), and immobilized lipase B from *C. antarctica* (Novozyme 435®), lipase from *R. miehei* and anthraquinone catalyst (90%) from Sigma Aldrich (St. Louis, Mo.).

Acid numbers of dry samples were evaluated according to the method of acid value, AOCS Te 1a-64. The hydroxyl number was evaluated according to the determination of hydroxyl numbers of polyols, ASTM 4274-05. The epoxy content of a dry sample was analyzed by an official method, AOCS Cd 9-57, oxirane oxygen.

Estolide Synthesis—To produce ricinoleic acid (RC) estolides, lipase from *C. rugosa* and immobilized lipase B from *C. antarctica* (Novozyme 435®) were used in the esterification without any organic solvent. The esterification takes place at temperatures of 40° and 60° C., and at pressures of 1 atm (open system) and 0.63 atm. Vacuum pressure (0.63 atm) was applied to remove water, an esterification product, and prevent the reversible reaction from taking place.

Ricinoleic acid had an acid number of 142 (mg KOH/g), which can be converted to the acid equivalent weight of about 395. Acid numbers of ricinoleic acid decreased when the fatty acid was kept at room temperature (22° C.) due to slowly condensation polymerization. To maintain the acid number of the hydroxy fatty acids, all samples were kept in the refrigerator (below 5° C.).

To start the esterification, enzyme *C. rugosa* (0.6 g) or Novozyme 435 (1 g) was combined with 15 g of ricinoleic acid fatty acid in a 125-Erlenmeyer flask and the operation mode was well-mixed batch. Three reactions were performed concurrently and the standard deviation was calculated.

After the reaction was performed (usually after 120 h), the immobilized enzyme was removed from the reaction product by centrifuge. Acetone was used to wash Novozyme 435® and the immobilized enzyme was reused for the next reaction after evaporating the acetone at 60° C.

Novozyme 435® was reused to investigate the enzyme's life time. The lipase was washed with acetone and dried after every reaction before being recycled.

Polyols with the higher hydroxyl equivalent weight were made by the cleavage of epoxy rings with fatty acid estolides. The fatty acid estolides were yielded from enzyme esterification of RC, as previously described. The RC estolide with acid number of 79 (produced under 60° C., 1 atm, 120 h by Novozyme 435®) was combined with ESBO, with the ratio of epoxy to acid being 1:0.66 by mole. The reaction took place in a batch well-mixed reactor at 170° C. and 1 atm until the acid number of polyols product was less than 10 (mg KOH/g).

Bodied Soybean Oil Synthesis—BSBO was produced by heating soybean oil with 2.5% of anthraquinone catalyst at 260° C. for 6 h. The bodying process was done in 1-liter Parr reactor with volatile matters being removed during the reaction by a venting channel. The solid catalyst was reusable and was removed from the BSBO by centrifugation. After 6 h, the bodying process increased the viscosity by 5.5 times and reduced the iodine number by 25%, with the viscosity and the iodine values for the bodied soybean oil being 313 mPa·s (at 22° C.) and 90, respectively.

BSBO was partially hydrolyzed by commercial lipases without any surfactant or organic solvent. The bodied soybean oil, phosphate buffer pH=7.0 (0.7 g/g oil), and *R. miehie* lipase (6.6 μl/g oil) were combined and mixed before the reaction started. The hydrolysis took place at 45° C. and 1 atm in a well mixed reactor for 3 days.

After the reaction, water and enzyme were separated from the oil phase by centrifuging (4000 rpm, 30 min). The product HBSBO had an acid number of about 83 (mg KOH/g). Examples of BSBO and HBSBO are displayed in FIG. 4. The HBSBO had acid functional groups with high MW and were furthered used to open the epoxy ring of EBSO.

HBSBO (acid number=83 mg KOH/g) was produced from the enzyme hydrolysis of BSBO which was previously described. The HBSBO and ESBO were combined with the ratio of epoxy per acid of 1:0.66. The reaction took place at 170° C. and 1 atm until the acid number was less than 10 (mg KOH/g). Acid number and epoxy content were determined against time.

Reaction Addition of Fatty Acids to Epoxy Soybean Oil—Linoleic acid (LA) and ricinoleic acid (RC) were used to open oxirane rings of epoxy soybean oil (ESBO). To perform the reaction, ESBO and LA (acid number=190 mg KOH/g), or ESBO and RC (acid number=142 mg KOH/g) were combined and reacted at 170° C. and at atmospheric pressure. The reaction was simply performed in a well-mixed batch reactor. Three ratios of epoxy functional group to acid functional group were used; 1:1, 1:0.8 and 1:0.5 by mole. Samples were collected with respect to time to measure acid number and epoxy content for the kinetic studies.

Summary of Product Properties—Acid equivalent weights of ricinoleic acid estolides synthesized by enzyme transesterification are shown in FIG. 5. The higher the reaction conversion is, the higher the acid equivalent weight is or the higher the average MW.

RC estolides produced from the recycled immobilized lipase,

Novozyme 435®, are presented in FIG. 5. The immobilized enzyme, Novozyme 435®, was recycled and used at 1 atm (600 and 70° C.), as a result (FIG. 5), the enzyme's activity and reactivity were still good after 7 times of recycling with a batch well-mixed operation (60-70° C.).

Typical properties reported for the commercial polyols are acid number, hydroxyl number, OH equivalent weight, MW, functionality, and viscosity. The apparent MW of soy-based polyols analyzed by gel permeation chromatography (GPC) was found to be higher than their real value due to their bulky molecular structure. The relative MW of soy-based polyols can be easily observed by their viscosity and OH numbers. The higher viscosity, the higher the MW. However, the OH and epoxy functional groups also increased the polyols' viscosity.

TABLE 11

Properties of polyols made from ESBO and vegetable oil based acid moieties.

| Acid moieties (acid number) | Ratio of epoxy to acid moieties | Properties of Polyols: Rxn time (h) | Acid # (mg KOH/g) | OH # (mg KOH/g) | OH Equ. weight | Epoxy wt % | Viscosity (22° C.) (mPa s) |
|---|---|---|---|---|---|---|---|
| LA | 1:1 | 17 | 25 | 76 | 740 | <0.1 | 1400 |
| (190) | 1:0.8 | 17 | 14 | 107 | 520 | <0.1 | 2540 |
| | 1:0.5 | 17 | 4 | 112 | 500 | 0.8 | 2860 |

TABLE 11-continued

Properties of polyols made from ESBO and vegetable oil based acid moieties.

| Acid moieties (acid number) | Ratio of epoxy to acid moieties | Properties of Polyols Rxn time (h) | Acid # (mg KOH/g) | OH # (mg KOH/g) | OH Equ. weight | Epoxy wt % | Viscosity (22° C.) (mPa s) |
|---|---|---|---|---|---|---|---|
| RC (142) | 1:1 | 13 | 16 | 159 | 350 | <0.1 | 9420 |
| | 1:0.8 | 13 | 16 | 163 | 340 | <0.1 | 8620 |
| | 1:0.5 | 10 | 5 | 152 | 370 | 0.2 | 7670 |
| RC estolide (79) | 1:0.66 | 6 | 8 | 109 | 520 | 0.3 | 5290 |
| HBSBO (83) | 1:0.66 | 6 | 10 | 82 | 680 | 0.3 | 3000 |
| Alkoxyl hydroxyl soybean oil (Sovermol ® 1068)* | | — | 0-3.9 | 180-205 | 270-310 | — | 3000-6000 (at 20° C.) |

*A commercial product and product's properties by Cognis Oleochemicals

Properties of high equivalent weight soy-based polyols produced from ESBO are shown in Table 11. Properties of a commercially available soy-based polyol, Sovermol® 1068 (alkoxyl hydroxyl soybean oil), are also shown in the same table.

Normally, the acid numbers of commercially available polyols are lower than 10 (mg KOH/g). An excess amount of epoxy group is needed to reduce the polyols' acid number because the possible side reactions could also take place.

Example 8

Flexible and Semi-Rigid Foams with Long Branch Groups—Foams were prepared using the formulations of Table 12. Table 13 reports the performance of these foams. Table 14 reports the preparation of the R10-R13 samples. The performance data indicates good performance for the R10-R13 performance, therein demonstrating the ability to use these soy-based polyols in flexible foam formulations.

TABLE 12

| Flexible foam formulations. |
|---|
| For 100% VORANOL 4701: |
| Voranol 4701: 100 parts by weight (pbw) |
| Water: 5.0 pbw |
| DABCO 33-LV: 0.3 pbw ® |
| DABCO BL-17: 0.2 pbw |
| Diethanolamine: 2.2 pbw |
| DABCO 2585: 0.5 pbw |
| PAPI 27: Index 80 |
| For 50% of soy-based polyols and 50% of VORANOL 4701: |
| Voranol 4701: 50 parts by weight (pbw) |
| Soy-based polyols: 50 pbw |
| Water: 5.0 pbw |
| DABCO 33-LV: 0.6 pbw |
| DABCO BL-17: 0.2 pbw |
| Stannous Octoate: 0.3 pbw |
| Dibutyltin Dilaurate: 0.3 pbw |
| Diethanolamine: 2.2 pbw |
| DABCO 2585: 1.0 pbw |
| PAPI 27: Index 80 |

TABLE 13

Performance of foams using formulations of Table 12. ESBO is epoxy soybean oil and LA is linoleic acid.

| | 1 Voranol 3136 | 2 Castor Oil | 3 SOVER MOL 1068 | 4 Batch 5 | 5 ESBO + LA − 4701 | 6 Voranol 4701 | 7 R10 + R11 + R12 + R13 | 8 R10 + R11 + R12 + R13 |
|---|---|---|---|---|---|---|---|---|
| OH Value | 54 | 160 | 180-205 | 192.5 | 118.2 | 34 | 113.61 | 113.61 |
| Isocyanate Index | 80 | 80 | 80 | 80 | 100 | 80 | 100 | 80 |
| Density (kg/m3) | 42.29 | 48.29 | 51.05 | 37.6 | 41.29 | 44.83 | 42.6 | 46.75 |
| CFD, 50% Deflection (kPa) | 15.47 | 31.65 | 27.65 | 13.4 | 38.22 | 8.78 | 19.73 | 11.59 |
| CDC, 50%, Ct = [(to − tf)/to] × 100 | 13.04 | 21.83 | 45.7 | 45.98 | 41.45 | 5.54 | 33.19 | 16.35 |
| Tear (N/m) | 149.21 | 241.32 | 332.56 | 188.54 | 256.94 | 142.4 | 187.22 | 153.73 |
| Resilience (%) | 46.36 | 19.83 | 18.22 | 16.78 | 36 | 44.89 | 34.44 | 36.78 |

TABLE 14

Properties and reaction conditions for R10-R13 epoxy soybean oil based polyol of Table 13. The acid is linoleic acid.

| | | Product properties | | | | |
|---|---|---|---|---|---|---|
| Epoxy:Acid (by mole) | Reaction conditions | Acid # (mg KOH/g) | OH # (mg KOH/g) | OH Equ. weight | Epoxy content (% by wt.) | Viscosity (22° C.) ($cm^2s^{-1}$) |
| 1:0.5 | 170° C./17 h | 4 | 112 | 500 | 0.8 | 2860 |

Bodied Oil with Epoxidation of Carbon-Carbon π-Bonds—An alternative embodiment of this invention is bodied soybean oil that is epoxidized to attach epoxy moieties. The bodied soybean oil may be prepared by the methods described earlier. Epoxidation is by ways known in the art.

Bodying of an unsaturated vegetable oil may be attained by maintaining the vegetable oil at a temperature greater than 180° C. for a time greater than one minute and until the ambient-temperature viscosity of the unsaturated vegetable oil is at least 25% greater than the viscosity prior to the bodying and partially oxidizing the bodied unsaturated vegetable oil.

Preferably the following applies. The unsaturated vegetable oil is soybean oil. The bodying step is without a catalyst and at a temperature between 240° and 360° C. The bodying step is performed at a temperature between 260° and 340° C. for a reaction time between 10 and 180 minutes.

More preferably, the following applies. The partially oxidizing step is an epoxidation reaction. The epoxidation is chemo-enzymatic epoxidation performed by enzyme catalysis including an immobilized lipase, hydrogen peroxide, soy-based fatty acids and organic solvent. The immobilized lipase is lipase B from *Candida antarctica* (Novozyme 435) and 8% to 9% (wt) of the immobilized lipase is used.

By example, the soy-based fatty acids are stearic acid or linoleic acid and 15% (wt) of the fatty acid is used. The organic solvent is toluene and (3-4 ml solvent/g oil) is used. The hydrogen peroxide is 30 to 50% solution and is excessively charged to obtain the complete epoxidation. The chemo-enzymatic epoxidation is carried out at room temperature for longer than 24 hours. The epoxidation is performed by a reaction including hydrogen peroxide and an organic acid.

Example 9

Epoxidized Soy-Based-Materials from Enzymatic Epoxidation Including Diglycerides—This example illustrates the synthesis of epoxy soybean oil. The chemicals for synthesis include refined soybean oil (food grade) from a local grocery store, linoleic acid (90%) from City Chemical LLC (West Heaven, Conn.), stearic acid (>90%), Novozyme 435® (immobilized lipase B from *Candida antarctica* on acrylic resin) from Sigma Aldrich (St. Louis, Mo.), and hydrogen peroxide solutions (30%) from Fisher (Houston, Tex.).

Well-Mixed Reactor—Soybean oil (5 g), linoleic acid (0.3 g) and toluene (10 ml) were combined in a 125-ml Erlenmeyer flask. Immobilized lipase, Novozyme 435®, (0.53 g) was added to the mixture when the reaction started. Hydrogen peroxide solution (30%) was added dropwise during the first 5 h of the reaction. Three ratios of hydrogen peroxide to C═C double bonds ($H_2O_2$:C═C) were used: 0.6, 0.8 and 1.0 by mole. The reaction further continued for 24 h in a controlled environment incubator shaker (PSYCROTHERM, New Brunswick, N.J.) at room temperature and the speed of 300 rpm.

Water, unreacted hydrogen peroxide, and immobilized enzyme were removed from the reaction product due to immiscibility of these materials in the oil phase. Fatty acid was removed by a saponification method. Either sodium dicarbonate, or sodium carbonate solution (0.5 N) was used to saponify the fatty acid after the reaction. After the saponification, the fatty acid soap was formed and stayed in the water phase. A centrifuge is also used to speed up the phase separation process. Toluene was finally removed from the epoxy soybean oil before measuring the epoxy content.

To study the effect of hydroperoxy on the enzyme's activity, the amount of hydrogen peroxide was varied; 0.6, 0.8 and 1.0 of $H_2O_2$:C═C by mole, which yielded an epoxy functionality of 2.8, 3.7, and 4.6 in complete epoxidation. The epoxidation conversion after the reaction was evaluated by the titration of epoxy weight percent and is shown in FIG. 6.

From FIG. 6 it can be seen that commercially available immobilized lipase B from *C. antarctica* (Novozyme 435®) was an effective biocatalyst in the epoxidation of soybean oil triglyceride. The reaction yielded over 90% conversion and the lipase was also reusable with high activity under some operating conditions.

In hexane or toluene, the lipase's activity was well maintained after four reuses when less hydrogen peroxide is used (0.6 mole ratio of $H_2O_2$:C═C). These data suggest that the hydroperoxide solution reduced the enzyme's activity and shorted the enzyme's life, as indicated by the decrease of the reaction conversion after three uses when the higher amount of hydrogen peroxide was used.

The organic solvents preserved the enzyme's activity. At 0.8 and 1.0 mole ratios of $H_2O_2$:C═C and without any solvent, the enzyme did not yield any significant conversion after two uses. Toluene and hexane gave comparable results until the second use of the enzyme.

Packed-Bed Reactor—The PBR design and operation of chemo-enzymatic epoxidation of soybean oil is illustrated in FIG. 7. Every 24 h, a small sample (100 μl-200 μl) in the mixing tank was drawn and reacted with tetramethylammonium hydroxide in methanol to prepare methyl ester derivatives of the epoxidized products ready for GC-analysis.

According to the operation of PBR producing epoxy soybean oil in FIG. 7, a sample was taken every 24 h for 72 h. GC-FID analysis was used to determine the percentage of each fatty acid methyl ester. It was found that the maximum disappearance of unsaturated fatty acids occurred after 48 h with the percent disappearance of linolenic, linoleic, and oleic acid at 62%, 51%, and 30%, respectively.

Among unsaturated fatty acids in soybean oil, the disappearing percentage of the linolenic acid (18:3) was highest, followed by the linoleic acid (18:2) and the oleic acid (18:1), respectively. However, the reaction yields produced from PBR were not as high as those produced from the well-mixed reactor. In addition, the epoxy fatty acid moieties were predominately mono-epoxy stearic acids, as analyzed by GC-FID. Hydrophilicity of the enzyme's support might cause poor mass transfer resulting in low epoxidation yield. To increase epoxidation yield by the PBR operation, a surfactant could be used to create a reverse micelle system and not deactivate the enzyme.

Chemo-Enzymatic Epoxidation of Blown Soybean Oil, Bodied Soybean Oil and Soy-Based Diglycerides—Soybean oil triglyceride has iodine number of 120 and 85% of unsaturated fatty acid. The epoxy content of epoxidized blown soybean oil, epoxidized bodied soybean oil and epoxidized soy-based diglycerides were evaluated by the titration method. The values were 3.8%, 5.5%, and 2.5% for soy-based diglyceride, bodied soybean oil, and blown soybean oil after chemo-enzymatic epoxidation versus 0.2%, 0.2%, and 0.8% before the reaction. For a reference, the complete epoxy soybean oil had 6.8-7.0% epoxy content (by wt).

Originally, the epoxy content in blown soybean oil was a little higher than in the other soy-based material. This is because blown soybean oil is the oxidized product from heat and oxygen gas. Blown soybean oil could have either epoxy or peroxy functional groups detected by the titration method. The production of bodied soybean oil was performed under $N_2$ gas environment where any oxidizing functional group should not be produced.

The iodine numbers of bodied soybean oil and soy-based diglyceride were comparable, and were about 55-58% of the iodine number of soybean oil triglyceride. However, the epoxidation product of bodied soybean oil was about 5.5% epoxy content and the epoxidation product of soy-based diglyceride is about 3.8% epoxy content.

Low reaction yield of the epoxidation of soy-based diglyceride was limited by the amount of hydrogen peroxide used, which was 0.5:1 of $H_2O_2$:C═C (by mole). From GC-analysis of ENOVA® oil, the substrate had C═C functionality of 3.4, which could be converted to 9% of epoxy content if the complete epoxidation was achieved.

As a result, the reaction conversion of the epoxidation of soy-based diglyceride under the described condition was about 76%. The reaction conversion was not changed when linoleic acid was replaced with formic acid, which is a common acid used in chemical route of the epoxidation.

Blown soybean oil had lower degrees of unsaturation, as indicated by the low iodine number. The epoxidized blown soybean oil, which was produced under the described conditions, contained 2.5% epoxy content.

Example 10

Flexible and Semi-Flexible Foams from Bodied SBO and Fatty Acid Addition Polyols—This example illustrates the synthesis of several flexible foams. Polyols were prepared as follows:

Sample F1—BSBO (100 grams, iodine value of 103.8) was mixed with 15 grams of Acetol and 14 grams DCP at 220° C. for 20 hours. The intermediate had an acid number of 48, iodine number of 106 (26% reduction) and OH number of 63. To this was added 16.2 grams of ESBO, which was reacted at 170° C. for 6 hours. The final polyol had an acid number of 7, epoxy content of 0.6%, and OH number of 98.

Sample F2—BSBO (100 grams, iodine value of 103.1) was mixed with 20 grams of Acetol and 14 grams DCP at 220° C. for 20 hours. The intermediate had an acid number of 55, iodine number of 104 (25% reduction) and OH number of 66. To this was added 14 grams of ESBO, which was reacted at 170° C. for 6 hours. The final polyol had an acid number of 4.6, epoxy content of 0.6%, and OH number of 101.

Sample F3—BSBO (100 grams, iodine value of 103.8) was mixed with 20 grams of Acetol and 14 grams DCP at 200° C. for 20 hours. The intermediate had an acid number of 52, iodine number of 111 (20% reduction) and OH number of 42. To this was added ESBO, which was reacted at 180° C. for 6 hours. The final polyol had an acid number of 6.3, epoxy content of 0.5%, and OH number of 95.

Sample F4—In an open reaction vessel mix: 50 grams Ricinoleic Acid (commercial Castor Oil) and 70.6 grams Epoxidized Soybean Oil (ESBO). The molar epoxy per acid ratio is 1:0.5. The mixture is heated to 170° C. for 16 hours under constant mixing (250 rpm).

Sample F5—In an open reaction vessel mix: 50 grams Linoleic Acid (commercial) and 79.7 grams ESBO. The molar epoxy per acid ratio is 1:0.5. The mixture is heated to 170° C. for 28 hours under constant mixing (250 rpm).

Sample F6—Bodied Soybean Oil (BSBO) was synthesized by reacting soybean oil (SBO) (about 600 g) and 2% by wt (based on SBO) Anthraquinone (catalyst) in a Parr reactor heated to 300° C. for 3.5 hours. The catalyst was removed from the product by centrifugation. Hydrolyzed bodied soybean oil (HBSBO) was synthesized by reacting 250 grams of BSBO and 500 grams distilled water in an open well-mixed batch reactor. About 0.5-1.0 gram of *C. rugosa* lipase powder was added to the reaction at 40° C. for 3 days or until 47.3% hydrolysis of the BSBO (Acid #=89.8) is obtained. HBSBO was collected and separated from the reaction products by centrifugation. Then, in a closed reaction vessel mix: 50 grams HBSBO and 7.4 grams 1,2-epoxybutane. The molar epoxy per acid ratio is 1:0.7. The mixture is heated to 170° C. for 20 hours under constant mixing (250 rpm).

Sample F7—The same as F6 except that the molar epoxy per acid ratio is 1:0.5 where 10.3 grams of 1,2-epoxybutane was added to 50 grams of HBSBO.

The properties of these soy-based polyols are summarized in Table 15. They were tested in the flexible foam recipe of Table 16. The properties of the foam are summarized in Table 17. These results indicate the successful synthesis of these polyols and use in a flexible foam formulation.

TABLE 15

Summary of soy-based polyols prepared for flexible foam formulation.

| | Acid No. | OH No. | Epoxy Content % | η (cP) |
|---|---|---|---|---|
| F1 | 7.08 | 97.7 | 0.57 | 3075 |
| F2 | 4.58 | 101.3 | 0.59 | 5570 |
| F3 | 6.27 | 95.0 | 0.48 | 3606 |
| F4 | 2.8 | 149.3 | 0.58 | 12540 |
| F5 | 1.4 | 145.1 | 0.67 | 7786 |
| F6 | 2.8 | 138.5 | <0.1 | 230.9 |
| F7 | 8.4 | 187.9 | 1.13 | 118.7 |

TABLE 16

Foam recipe used to make foams from soy-based polyols of Table 15

| Ingredients | Parts by weight |
|---|---|
| B-side materials | |
| VORANOL ® 4701 | 50 |
| Vegetable Oil based Polyol | 50 |
| Dabco 33-LV ® | 0.6 |
| Dabco ® BL-17 | 0.2 |
| Dabco ® DC 2585 | 1.0 |
| Diethanolamine | 2.2 |
| Stannous Octoate | 0.3 |
| Dibutyltin Dilaurate | 0.3 |
| Blowing Agent (distilled water) | 5.0 |
| A-side material | |
| PAPI ® 27 | Index 80 |

TABLE 18

Impact of temperature and residence time in flow reactor on bodying of soybean oil in the absence of catalyst or cross-linker.

| Samples | Temperature (° C.) | Flow rate mL/s | Retention time (Min) | Iodine No. | Acid No. |
|---|---|---|---|---|---|
| B1 | 350 | 0.1 | 83.3 | 109.1 | 19.1 |
| B2 | 350 | 0.1 | 83.3 | 106.9 | 18.1 |
| B3 | 350 | 0.1 | 83.3 | 105.9 | 19.8 |
| B4 | 350 | 0.043 | 193.8 | 100.9 | 26.3 |
| B5 | 350 | 0.043 | 193.8 | 103.6 | 21.2 |
| B6 | 350 | 0.089 | 93.7 | 99.6 | 22.3 |
| B7 | 350 | 0.089 | 93.7 | 101.7 | 21.5 |

All bodied products had a viscosity of about 68 cp. Note: Reactor Volume 500 ml.

Note:

Viscosity 68 MPa-s (viscosity don't has significant change).

TABLE 17

Properties of foam produced from Soy-based polyols of Table 15.

| | OH Value | Iso Index | Density (kg/m$^3$) | CFD 50% Deflection (kPa) | CDC 50%, $C_t = [(t_o - t_f)/t_o] \times 100$ | Tear (N/m) | Resilience (%) |
|---|---|---|---|---|---|---|---|
| F1 | 104.7 | 80 | 51.4 | 16.13 | 27.29 | 172.8 | 28.0 |
| F2 | 105.9 | 80 | 42.4 | 13.59 | 32.41 | 192.3 | 27.6 |
| F3 | 105.0 | 80 | 59.7 | 22.66 | 32.08 | 200.7 | 27.0 |
| F4 | 152.1 | 80 | 38.4 | 17.87 | 43.43 | 167.9 | 22.3 |
| F5 | 120.1 | 80 | 45.8 | 12.15 | 28.30 | 169.2 | 35.3 |
| F6 | 141.3 | 80 | 46.2 | 12.43 | 35.06 | 159.4 | 28.0 |
| F7 | 196.3 | 80 | 37.4 | 8.59 | 44.46 | 141.5 | 24.3 |

In the embodiments of this invention, 9-10 Anthraquinone was used as a catalyst while dicylopendatiene and divinylbenzene were used as cross-linkers to promote the formation of oligomers that can be functionalized to form B-side prepolymers. These oligomers preferably have an average molecular weight of between 900 and 20,000, and more preferably between 1300 and 5,000. The oligomers themselves have multiple applications, including use as precursors for functionalizing, use as prepolymers, and use as binders. The bodied oil embodiments are presented by way of the following illustrative example.

Example 11

Bodying of Soybean Oil Including Binder Applications—The combination of time and temperature is sufficient to body soybean oil as is illustrated by the data of Table 18. Indications of the bodying reaction include a decrease in iodine number (starting at 134-135 with soybean oil) and an increase in viscosity (starting at about 52 with soybean oil). The data of Table 19 illustrate how 9-10 Anthraquinone allows the use of lower temperatures to achieve viscosities (degrees of polymerization) that are very difficult to obtain in the absence of a catalyst. The lower temperatures tend to preserve the quality of the bodied soybean oil where quality is indicated by lower odor and less color.

TABLE 19

Impact of 9-10 Anthraquinone no bodying of soybean oil in a batch reactor.

| Sample | Temperature (° C.) | Time (hrs) | Iodine No | Acid No. | Viscosity mPa-s (cP) |
|---|---|---|---|---|---|
| SBO no rxn. | — | — | 135 | 5 | 52 |
| BSBO no catalyst | 330 | 1 | 100 | 15 | 68 |
| BSBO catalyzed with AQ | 260 | 6 | 104 | 15 | 253 |
| BSBO catalyzed with AQ | 280 | 6 | 91 | 15 | 1158 |
| BSBO catalyzed with AQ | 300 | 6 | 70.5 | 15 | 2998 |

Note:

Catalyst: 9-10 Anthraquinone was using 2.5 to 5% wt. Reactor volume 2 liter.

Experiments were preformed to understand how dicylopendatiene and divinylbenzene cross-linkers further increase the crosslinking, leading to the formation of soft to very hard solids. The conditions are more-severe than desired for oligomer formation. Soybean oil was first mixed with varying amounts divinyl benzene, dicyclopendaiene dimer, and boron triflouride diethyl ether complex to form a prepolymer. The mixture was heated at 120° C. in an oven for about 18 hours. Tables 21 through 23 illustrate the impact of the crosslinkers and boron trifluoride catalyst on promoting reaction at lower temperatures.

TABLE 20

Effect of varying dicylopendatiene and divinylbenzene amounts on the final polymer.

| SBO g | Dicyclo-pentadiene g | Divinyl-benzene g | Boron Trifluoride g | Appearance & State |
|---|---|---|---|---|
| 6.506 | 0 | 3.011 | 0.5 | Hard |
| 6.501 | 0.501 | 2.501 | 0.505 | Very Hard |
| 6.501 | 1.003 | 2.008 | 0.507 | Hard |
| 6.501 | 1.5 | 1.503 | 0.502 | Hard |
| 6.5 | 2.003 | 1.002 | 0.516 | Hard |
| 6.501 | 2.5 | 0.5 | 0.508 | Soft & Rubbery |
| 6.5 | 3 | 0 | 0.509 | Very Soft & Rubbery |

TABLE 21

Effect of divinyl benzene amount on final polymer properties.

| SBO g | Dicyclo-pentadiene g | Divinyl-benzene g | Boron Trifluoride g | Appearance & State |
|---|---|---|---|---|
| 7.002 | 0 | 3.004 | 0.515 g | Very Hard |
| 7.5 | 0 | 2.51 | 0.523 g | Hard |
| 8.019 | 0 | 2.01 | 0.522 g | Soft |
| 8.507 | 0 | 1.506 | 0.504 g | Soft |
| 9 | 0 | 1.007 | 0.502 g | Soft & Rubbery |
| 9.504 | 0 | 0.505 | 0.532 g | Very Soft |

TABLE 22

Effect of catalyst on final polymer properties.

| SBO g | Dicyclo-pentadiene g | Divinylbenzene g | Boron Trifluoride g | Appearance & State |
|---|---|---|---|---|
| 6.507 | 0 | 3.012 | 0.52 | Very Hard |
| 6.504 | 0 | 3.008 | 0.42 | Very Hard |
| 6.505 | 0 | 3 | 0.3 | Very Hard |
| 6.503 | 0 | 3.018 | 0.2 | Hard |
| 6.506 | 0 | 3.005 | 0.1 | Hard |
| 6.505 | 0 | 3.001 | 0.05 | Soft |

The invention claimed is:

1. A process for preparing a polymeric polyol from a plurality of unsaturated triglycerides, the process comprising:

(a) bodying the plurality of unsaturated triglycerides at a temperature between 150° and 350° C. to form a bodied product, the bodying occurring in an environment where diatomic oxygen is substantially absent; and (b) contacting the bodied product with at least one monomer containing an oxygen-containing moiety, wherein hydroxyl groups are added directly to at least one carbon-carbon π-bond in the bodied product, thereby forming the polymeric polyol.

2. The process of claim 1, wherein the plurality of unsaturated triglycerides comprises a vegetable oil.

3. The process of claim 1, wherein the monomer containing the oxygen-containing moiety is selected from the group consisting of acetol, allyl alcohol, glycerin, glycols, epichlorohydrin, and acrolein; and the pressure is between 3 and 30 bars.

4. The process of claim 1, wherein the polymeric polyol has an acid number greater than 20 mg KOH/g and is reacted with an epoxy containing molecule to reduce the acid number to a value less than 15 mg KOH/g.

5. The process of claim 4, wherein the epoxy-containing molecule is epoxy soybean oil and the reaction with epoxy soybean oil is at a temperature between 140° and 190° C. without a catalyst.

6. The process of claim 1, wherein step (a) further comprises at least one catalyst, the catalyst being selected from the group consisting of an anthracene catalyst or a derivative thereof, and an organic catalyst with at least one ketone moiety and at least one carbon-carbon π-bond moiety, wherein the catalyst is a solid at temperatures below 100° C., the catalyst is present at a concentration between 2% and 10% (wt), and the catalyst can be separated for recycle as a solid from a liquid bodied product.

7. The process of claim 1, wherein step (a) further comprises a cross-linking monomer selected from the group consisting of dicyclopentadiene and divinylbenzene.

8. The process of claim 1 wherein step (b) is performed after step (a).

9. The process of claim 8, wherein the monomer containing the oxygen-containing moiety is acetol and the temperature of step (b) is between 180° and 250° C.

10. The process of claim 8, wherein the monomer containing the oxygen-containing moiety is allyl alcohol and the temperature of step (b) is between 240° and 340° C.

11. The process of claim 1, wherein step (a) and step (b) are performed simultaneously.

12. The process of claim 11, wherein the monomer containing the oxygen-containing moiety is acetol and the temperature is between 160° and 280° C.

13. The process of claim 11, wherein the monomer containing the oxygen-containing moiety is allyl alcohol and the temperature is between 240° and 340° C.

* * * * *